US006790938B1

(12) United States Patent
Berchtold et al.

(10) Patent No.: US 6,790,938 B1
(45) Date of Patent: Sep. 14, 2004

(54) ANTI-GPIIB/IIIA RECOMBINANT ANTIBODIES

(75) Inventors: Peter Berchtold, Schwetz (CH); Robert F. A. Escher, Schwetz (CH)

(73) Assignee: ASAT AG Applied Science & Technology, Zug (CH)

( * ) Notice: Subject to any disclaimer, the term of this patent is extended or adjusted under 35 U.S.C. 154(b) by 0 days.

(21) Appl. No.: 09/424,840

(22) PCT Filed: Jun. 5, 1998

(86) PCT No.: PCT/EP98/03397

§ 371 (c)(1),
(2), (4) Date: Dec. 3, 1999

(87) PCT Pub. No.: WO98/55619

PCT Pub. Date: Dec. 10, 1998

(30) Foreign Application Priority Data

Jun. 6, 1997 (DE) .......................... 197 23 904
Dec. 12, 1997 (DE) .......................... 197 55 227
May 8, 1998 (DE) .......................... 198 20 663

(51) Int. Cl.$^7$ .............................................. C07K 16/00
(52) U.S. Cl. .............................. 530/388.22; 530/387.1; 530/388.85; 424/130.1
(58) Field of Search ................................. 530/300, 350, 530/387.1, 388.1, 388.22, 388.85, 389.1, 391.2; 435/188; 429/130.1

(56) References Cited

U.S. PATENT DOCUMENTS 6,274,143 B1 * 8/2001 Chatterjee et al.

FOREIGN PATENT DOCUMENTS

| EP | 0 557 535 | 9/1993 |
| EP | 0 619 324 | 10/1994 |
| WO | 90 06134 | 6/1990 |
| WO | WO 98/55146 | 12/1998 |

OTHER PUBLICATIONS

Berchtold et al., Blood 74:2414–17, 1989.*
Nugent et al., Blood 70:16022, 1987.*
Rudikoff et al., PNAS 79:1979–83, 1982.*
Amit et al Science 233:747, 1986.*
Kunicki et al, J. Autoimmun 4:433–446, 1991.*
Horn et al., "ID:Q99506;AC:Q99506", Database EMBL, May 1, 1997.
Combriato G. et al., "Accession No. S25752", Database PIR2, 1993, & Eur. J. Immunol. (1991) 21: 1513–1522.
Escher R. et al., "Recombinant Human Natural Autoantibodies Against GPIIb/IIIa Inhibit Binding of Autoantibodies from Patients with AITP", Brit. J. Haematol., vol. 102, No. 3, Aug. 1998, pp. 820–828.

* cited by examiner

*Primary Examiner*—Larry R. Helms
(74) *Attorney, Agent, or Firm*—Rothwell, Figg, Ernst & Manbeck, P.C.

(57) ABSTRACT

The invention relates to novel nucleic acid sequences which encode human autoantibodies and antiidiotypic antibodies against blood platelet membrane proteins, to novel amino acid sequences of human antibodies, and to their use for the diagnosis and therapy of diseases.

5 Claims, 7 Drawing Sheets

SEQUENCE LISTING

<160> NUMBER OF SEQ ID NOS: 128

<210> SEQ ID NO 1
<211> LENGTH: 357
<212> TYPE: DNA
<213> ORGANISM: Homo sapiens
<220> FEATURE:
<221> NAME/KEY: CDS
<222> LOCATION: (1)..(357)
<223> OTHER INFORMATION:

<400> SEQUENCE: 1

```
cag gtg aaa ctg ctc gag tcg ggc cca gga ctg gtg aag cct tcg gag      48
Gln Val Lys Leu Leu Glu Ser Gly Pro Gly Leu Val Lys Pro Ser Glu
1               5                   10                  15 acc ctg tcc ctc aac tgc act gtc tct ggt cgc tcc atc agt ggt tac      96
Thr Leu Ser Leu Asn Cys Thr Val Ser Gly Arg Ser Ile Ser Gly Tyr
            20                  25                  30 tct tgg aga tgg atc cgg cag tct cca ggg aag gga cta gag tgg att     144
Ser Trp Arg Trp Ile Arg Gln Ser Pro Gly Lys Gly Leu Glu Trp Ile
        35                  40                  45 ggg gat atc tct tat agt ggg agt acc aag tac aaa ccc tcc ctc agg     192
Gly Asp Ile Ser Tyr Ser Gly Ser Thr Lys Tyr Lys Pro Ser Leu Arg
    50                  55                  60 agt cga gtc acc ctg tca gta gac acg tcc aag aac cag ttc tcc ctg     240
Ser Arg Val Thr Leu Ser Val Asp Thr Ser Lys Asn Gln Phe Ser Leu
65                  70                  75                  80 aag ctg aat tcg gtg acc gct gcg gac acg gcc gtc tat tac tgt gcg     288
Lys Leu Asn Ser Val Thr Ala Ala Asp Thr Ala Val Tyr Tyr Cys Ala
                85                  90                  95 cga gtc ttg ccc ttt gac ccg atc tcg atg gac gtc tgg ggc aaa ggg     336
Arg Val Leu Pro Phe Asp Pro Ile Ser Met Asp Val Trp Gly Lys Gly
            100                 105                 110 acc acg gtc acc gtc tcc tca                                         357
Thr Thr Val Thr Val Ser Ser
        115
```

<210> SEQ ID NO 2
<211> LENGTH: 119
<212> TYPE: PRT
<213> ORGANISM: Homo sapiens

<400> SEQUENCE: 2

```
Gln Val Lys Leu Leu Glu Ser Gly Pro Gly Leu Val Lys Pro Ser Glu
1               5                   10                  15

Thr Leu Ser Leu Asn Cys Thr Val Ser Gly Arg Ser Ile Ser Gly Tyr
```

-continued

```
                         20                  25                  30
Ser Trp Arg Trp Ile Arg Gln Ser Pro Gly Lys Gly Leu Glu Trp Ile
             35                  40                  45

Gly Asp Ile Ser Tyr Ser Gly Ser Thr Lys Tyr Lys Pro Ser Leu Arg
         50                  55                  60

Ser Arg Val Thr Leu Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                 85                  90                  95

Arg Val Leu Pro Phe Asp Pro Ile Ser Met Asp Val Trp Gly Lys Gly
            100                 105                 110

Thr Thr Val Thr Val Ser Ser
            115

<210> SEQ ID NO 3
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION:

<400> SEQUENCE: 3 gtg gtg act cag cca ccc tca gcg tct ggg acc ccc ggg cag tgg gtc      48
Val Val Thr Gln Pro Pro Ser Ala Ser Gly Thr Pro Gly Gln Trp Val
 1               5                  10                  15 acc atc tct tgt tct ggg agc agc tcc aac atc aga agt aat cct gtt      96
Thr Ile Ser Cys Ser Gly Ser Ser Ser Asn Ile Arg Ser Asn Pro Val
             20                  25                  30 agc tgg tat cac cag gtc cca ggc acg gcc ccc aaa ctc ctc atc ttt     144
Ser Trp Tyr His Gln Val Pro Gly Thr Ala Pro Lys Leu Leu Ile Phe
         35                  40                  45 ggt agt cat cag cgg ccc tca ggg gtc cct gac cga ttc tct ggc tcc     192
Gly Ser His Gln Arg Pro Ser Gly Val Pro Asp Arg Phe Ser Gly Ser
     50                  55                  60 aag tcg ggc acc tcc gcc tcc ctg gcc atc cgt ggg ctc caa tct ggg     240
Lys Ser Gly Thr Ser Ala Ser Leu Ala Ile Arg Gly Leu Gln Ser Gly
 65                  70                  75                  80 gat gct ggt gac tat tac tgt gca aca tgg gat gac ggc ctc aat ggt     288
Asp Ala Gly Asp Tyr Tyr Cys Ala Thr Trp Asp Asp Gly Leu Asn Gly
                 85                  90                  95 ccg gtg ttc ggc gga ggg acc aag ctg acc gtc cta agt cag ccc         333
Pro Val Phe Gly Gly Gly Thr Lys Leu Thr Val Leu Ser Gln Pro
            100                 105                 110

<210> SEQ ID NO 4
<211> LENGTH: 111
<212> TYPE: PRT
<213> ORGANISM: Homo sapiens

<400> SEQUENCE: 4

Val Val Thr Gln Pro Pro Ser Ala Ser Gly Thr Pro Gly Gln Trp Val
 1               5                  10                  15

Thr Ile Ser Cys Ser Gly Ser Ser Ser Asn Ile Arg Ser Asn Pro Val
             20                  25                  30

Ser Trp Tyr His Gln Val Pro Gly Thr Ala Pro Lys Leu Leu Ile Phe
         35                  40                  45

Gly Ser His Gln Arg Pro Ser Gly Val Pro Asp Arg Phe Ser Gly Ser
     50                  55                  60
```

```
Lys Ser Gly Thr Ser Ala Ser Leu Ala Ile Arg Gly Leu Gln Ser Gly
 65                  70                  75                  80

Asp Ala Gly Asp Tyr Tyr Cys Ala Thr Trp Asp Asp Gly Leu Asn Gly
                 85                  90                  95

Pro Val Phe Gly Gly Gly Thr Lys Leu Thr Val Leu Ser Gln Pro
            100                 105                 110

<210> SEQ ID NO 5
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION:

<400> SEQUENCE: 5 cag gtg aaa ctg ctc gag tct ggg gga ggc gtg gtc cag cct ggg agg      48
Gln Val Lys Leu Leu Glu Ser Gly Gly Gly Val Val Gln Pro Gly Arg
1               5                   10                  15 tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
            20                  25                  30 gct atg cac tgg gtc cgc cag gct cca ggc aag ggg ctg gag tgg gtg     144
Ala Met His Trp Val Arg Gln Ala Pro Gly Lys Gly Leu Glu Trp Val
        35                  40                  45 gca gtt ata tca tat gat gga agc aat aaa tac tac gca gac tcc gtg     192
Ala Val Ile Ser Tyr Asp Gly Ser Asn Lys Tyr Tyr Ala Asp Ser Val
    50                  55                  60 aag ggc cga ttc gcc atc tcc aga gac aat tcc aag aac acg ctg tat     240
Lys Gly Arg Phe Ala Ile Ser Arg Asp Asn Ser Lys Asn Thr Leu Tyr
65                  70                  75                  80 ctg caa atg aac agc ctg aga gct gag gac acg gct gtg tat tac tgt     288
Leu Gln Met Asn Ser Leu Arg Ala Glu Asp Thr Ala Val Tyr Tyr Cys
                85                  90                  95 gcg aga gcg ctg ggg agc tgg ggg ggt tgg gac cac tac atg gac gtc     336
Ala Arg Ala Leu Gly Ser Trp Gly Gly Trp Asp His Tyr Met Asp Val
            100                 105                 110 tgg ggc aaa ggg acc acg gtc acc gtc tcc tca                         369
Trp Gly Lys Gly Thr Thr Val Thr Val Ser Ser
        115                 120

<210> SEQ ID NO 6
<211> LENGTH: 123
<212> TYPE: PRT
<213> ORGANISM: Homo sapiens

<400> SEQUENCE: 6

Gln Val Lys Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Ala Leu Gly Ser Trp Gly Trp Asp His Tyr Met Asp Val
            100                 105                 110
Trp Gly Lys Gly Thr Thr Val Thr Val Ser Ser
        115                 120
```

<210> SEQ ID NO 7
<211> LENGTH: 333
<212> TYPE: DNA
<213> ORGANISM: Homo sapiens
<220> FEATURE:
<221> NAME/KEY: CDS
<222> LOCATION: (1)..(333)
<223> OTHER INFORMATION:

<400> SEQUENCE: 7

```
gtg gtg act cag cca ccc tca gcg tct ggg acc ccc ggg cag agg gtc      48
Val Val Thr Gln Pro Pro Ser Ala Ser Gly Thr Pro Gly Gln Arg Val
1               5                   10                  15 acc atc tct tgt tct gga agc agc tcc aac atc gga agt aat act gta      96
Thr Ile Ser Cys Ser Gly Ser Ser Ser Asn Ile Gly Ser Asn Thr Val
                20                  25                  30 aac tgg tac cag cag ctc cca gga acg gcc ccc aaa ctc ctc atc tat     144
Asn Trp Tyr Gln Gln Leu Pro Gly Thr Ala Pro Lys Leu Leu Ile Tyr
            35                  40                  45 agt aat aat cag cgg ccc tca ggg gtc cct gac cga ttc tct ggc tcc     192
Ser Asn Asn Gln Arg Pro Ser Gly Val Pro Asp Arg Phe Ser Gly Ser
    50                  55                  60 aag tct ggc acc tca gcc tcc ctg gcc atc agt ggg ctc cag tct gag     240
Lys Ser Gly Thr Ser Ala Ser Leu Ala Ile Ser Gly Leu Gln Ser Glu
65                  70                  75                  80 gat gag gct gat tat tac tgt gca gca tgg gat gac agc ctg aat ggt     288
Asp Glu Ala Asp Tyr Tyr Cys Ala Ala Trp Asp Asp Ser Leu Asn Gly
                85                  90                  95 tgg gtg ttc ggc gga ggg acc aag ctg acc gtc cta ggt cag ccc         333
Trp Val Phe Gly Gly Gly Thr Lys Leu Thr Val Leu Gly Gln Pro
            100                 105                 110
```

<210> SEQ ID NO 8
<211> LENGTH: 111
<212> TYPE: PRT
<213> ORGANISM: Homo sapiens

<400> SEQUENCE: 8

```
Val Val Thr Gln Pro Pro Ser Ala Ser Gly Thr Pro Gly Gln Arg Val
1               5                   10                  15

Thr Ile Ser Cys Ser Gly Ser Ser Ser Asn Ile Gly Ser Asn Thr Val
                20                  25                  30

Asn Trp Tyr Gln Gln Leu Pro Gly Thr Ala Pro Lys Leu Leu Ile Tyr
            35                  40                  45

Ser Asn Asn Gln Arg Pro Ser Gly Val Pro Asp Arg Phe Ser Gly Ser
    50                  55                  60

Lys Ser Gly Thr Ser Ala Ser Leu Ala Ile Ser Gly Leu Gln Ser Glu
65                  70                  75                  80

Asp Glu Ala Asp Tyr Tyr Cys Ala Ala Trp Asp Asp Ser Leu Asn Gly
                85                  90                  95

Trp Val Phe Gly Gly Gly Thr Lys Leu Thr Val Leu Gly Gln Pro
            100                 105                 110
```

<210> SEQ ID NO 9
<211> LENGTH: 369

<212> TYPE: DNA
<213> ORGANISM: Homo sapiens
<220> FEATURE:
<221> NAME/KEY: CDS
<222> LOCATION: (1)..(369)
<223> OTHER INFORMATION:

<400> SEQUENCE: 9

```
cag gtg aaa ctg ctc gag tct ggg gga ggc ttg gtt cac ccc ggg ggg     48
Gln Val Lys Leu Leu Glu Ser Gly Gly Gly Leu Val His Pro Gly Gly
1               5                   10                  15 tcc ctg aga ctc tct tgt gca gcc tct gga ttt acg ttt gac aac ttt     96
Ser Leu Arg Leu Ser Cys Ala Ala Ser Gly Phe Thr Phe Asp Asn Phe
            20                  25                  30 gcc atg agc tgg gtc cgc cag gct cca ggg aag ggg ctg gag tgg gtc    144
Ala Met Ser Trp Val Arg Gln Ala Pro Gly Lys Gly Leu Glu Trp Val
        35                  40                  45 tca ggc att agt ggt ggt ggt ctt ttg aca cac tac gca gac tcc gtg    192
Ser Gly Ile Ser Gly Gly Gly Leu Leu Thr His Tyr Ala Asp Ser Val
    50                  55                  60 aag ggc cgg ttc acc atc tcc aga aac aat tcc agg aac act gta tac    240
Lys Gly Arg Phe Thr Ile Ser Arg Asn Asn Ser Arg Asn Thr Val Tyr
65                  70                  75                  80 cta caa atg aac agc ctg aga gcc gaa gac acg gcc gtg tat tat tgt    288
Leu Gln Met Asn Ser Leu Arg Ala Glu Asp Thr Ala Val Tyr Tyr Cys
                85                  90                  95 gtg aga gat ctg ggc tat aga gta ctt tcg act ttt act ttt gat atc    336
Val Arg Asp Leu Gly Tyr Arg Val Leu Ser Thr Phe Thr Phe Asp Ile
            100                 105                 110 tgg ggc cag ggg aca aag gtc acc gtc tct tca                        369
Trp Gly Gln Gly Thr Lys Val Thr Val Ser Ser
        115                 120
```

<210> SEQ ID NO 10
<211> LENGTH: 123
<212> TYPE: PRT
<213> ORGANISM: Homo sapiens

<400> SEQUENCE: 10

```
Gln Val Lys Leu Leu Glu Ser Gly Gly Gly Leu Val His Pro Gly Gly
1               5                   10                  15

Ser Leu Arg Leu Ser Cys Ala Ala Ser Gly Phe Thr Phe Asp Asn Phe
            20                  25                  30

Ala Met Ser Trp Val Arg Gln Ala Pro Gly Lys Gly Leu Glu Trp Val
        35                  40                  45

Ser Gly Ile Ser Gly Gly Gly Leu Leu Thr His Tyr Ala Asp Ser Val
    50                  55                  60

Lys Gly Arg Phe Thr Ile Ser Arg Asn Asn Ser Arg Asn Thr Val Tyr
65                  70                  75                  80

Leu Gln Met Asn Ser Leu Arg Ala Glu Asp Thr Ala Val Tyr Tyr Cys
                85                  90                  95

Val Arg Asp Leu Gly Tyr Arg Val Leu Ser Thr Phe Thr Phe Asp Ile
            100                 105                 110

Trp Gly Gln Gly Thr Lys Val Thr Val Ser Ser
        115                 120
```

<210> SEQ ID NO 11
<211> LENGTH: 375
<212> TYPE: DNA
<213> ORGANISM: Homo sapiens
<220> FEATURE:

```
<221> NAME/KEY: CDS
<222> LOCATION: (1)..(375)
<223> OTHER INFORMATION:

<400> SEQUENCE: 11 gtg gtg act cag cct gcc tcc gtg tct ggg tct cct gga cag tcg atc      48
Val Val Thr Gln Pro Ala Ser Val Ser Gly Ser Pro Gly Gln Ser Ile
1               5                  10                  15 acc atc tcc tgc act gga acc agc agt gct att ggg aat tat aac ttt      96
Thr Ile Ser Cys Thr Gly Thr Ser Ser Ala Ile Gly Asn Tyr Asn Phe
            20                  25                  30 gtc ccc tgg tac caa cag cac cca ggc aaa gcc ccc aaa ctc atg att     144
Val Pro Trp Tyr Gln Gln His Pro Gly Lys Ala Pro Lys Leu Met Ile
        35                  40                  45 tat gag ggc agt aag cgg ccc tca ggg gtt tct aat cgc ttc tct ggc     192
Tyr Glu Gly Ser Lys Arg Pro Ser Gly Val Ser Asn Arg Phe Ser Gly
    50                  55                  60 tcc aag tct ggc aac acg gcc tcc ctg aca atc tct ggg ctc cag gct     240
Ser Lys Ser Gly Asn Thr Ala Ser Leu Thr Ile Ser Gly Leu Gln Ala
65                  70                  75                  80 gag gac gag gct gag tat tac tgc tgc tca tat gtt cat agt agc act     288
Glu Asp Glu Ala Glu Tyr Tyr Cys Cys Ser Tyr Val His Ser Ser Thr
                85                  90                  95 aat tgg gtg ttc ggc gga ggg acc aag ctg acc gtc cta ggt cag ccc     336
Asn Trp Val Phe Gly Gly Gly Thr Lys Leu Thr Val Leu Gly Gln Pro
            100                 105                 110 aag gct gcc ccc tcg gtc act ctg ttc cca ccc tcc tct                 375
Lys Ala Ala Pro Ser Val Thr Leu Phe Pro Pro Ser Ser
        115                 120                 125

<210> SEQ ID NO 12
<211> LENGTH: 125
<212> TYPE: PRT
<213> ORGANISM: Homo sapiens

<400> SEQUENCE: 12

Val Val Thr Gln Pro Ala Ser Val Ser Gly Ser Pro Gly Gln Ser Ile
1               5                  10                  15

Thr Ile Ser Cys Thr Gly Thr Ser Ser Ala Ile Gly Asn Tyr Asn Phe
            20                  25                  30

Val Pro Trp Tyr Gln Gln His Pro Gly Lys Ala Pro Lys Leu Met Ile
        35                  40                  45

Tyr Glu Gly Ser Lys Arg Pro Ser Gly Val Ser Asn Arg Phe Ser Gly
    50                  55                  60

Ser Lys Ser Gly Asn Thr Ala Ser Leu Thr Ile Ser Gly Leu Gln Ala
65                  70                  75                  80

Glu Asp Glu Ala Glu Tyr Tyr Cys Cys Ser Tyr Val His Ser Ser Thr
                85                  90                  95

Asn Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser
        115                 120                 125

<210> SEQ ID NO 13
<211> LENGTH: 366
<212> TYPE: DNA
<213> ORGANISM: Homo sapiens
<220> FEATURE:
<221> NAME/KEY: CDS
<222> LOCATION: (1)..(366)
<223> OTHER INFORMATION:
```

<400> SEQUENCE: 13

```
cag gtg aaa ctg ctc gag tca gga cca gga ctg gtg aag ccc tcg gag        48
Gln Val Lys Leu Leu Glu Ser Gly Pro Gly Leu Val Lys Pro Ser Glu
1               5                   10                  15 acc ctg tct ctc acc tgc act gtc tct gat gtc tcc atc aga agt cat        96
Thr Leu Ser Leu Thr Cys Thr Val Ser Asp Val Ser Ile Arg Ser His
            20                  25                  30 tac tgg agt tgg ctc cgg cag ccc cca ggg aag gga ctg gag tgg att       144
Tyr Trp Ser Trp Leu Arg Gln Pro Pro Gly Lys Gly Leu Glu Trp Ile
        35                  40                  45 ggg ttt atc tat gac ggt gcg aga acc agg ttc aac ccc tcc ctc agg       192
Gly Phe Ile Tyr Asp Gly Ala Arg Thr Arg Phe Asn Pro Ser Leu Arg
    50                  55                  60 agt cga gtc tcc ctt tca atg gac cca tcc aag aag cag ttt tcc ctg       240
Ser Arg Val Ser Leu Ser Met Asp Pro Ser Lys Lys Gln Phe Ser Leu
65                  70                  75                  80 aaa ctg ggg tct gtg acc gct gcg gac tcg gcc gtc tac tac tgt gcg       288
Lys Leu Gly Ser Val Thr Ala Ala Asp Ser Ala Val Tyr Tyr Cys Ala
                85                  90                  95 aga gac gcg gat gga gat ggc ttc agc cca tac tac ttt ccc tac tgg       336
Arg Asp Ala Asp Gly Asp Gly Phe Ser Pro Tyr Tyr Phe Pro Tyr Trp
            100                 105                 110 ggc cag gga atc ccg gtc tcc gtc tcc tcg                               366
Gly Gln Gly Ile Pro Val Ser Val Ser Ser
        115                 120
```

<210> SEQ ID NO 14
<211> LENGTH: 122
<212> TYPE: PRT
<213> ORGANISM: Homo sapiens

<400> SEQUENCE: 14

```
Gln Val Lys Leu Leu Glu Ser Gly Pro Gly Leu Val Lys Pro Ser Glu
1               5                   10                  15

Thr Leu Ser Leu Thr Cys Thr Val Ser Asp Val Ser Ile Arg Ser His
            20                  25                  30

Tyr Trp Ser Trp Leu Arg Gln Pro Pro Gly Lys Gly Leu Glu Trp Ile
        35                  40                  45

Gly Phe Ile Tyr Asp Gly Ala Arg Thr Arg Phe Asn Pro Ser Leu Arg
    50                  55                  60

Ser Arg Val Ser Leu Ser Met Asp Pro Ser Lys Lys Gln Phe Ser Leu
65                  70                  75                  80

Lys Leu Gly Ser Val Thr Ala Ala Asp Ser Ala Val Tyr Tyr Cys Ala
                85                  90                  95

Arg Asp Ala Asp Gly Asp Gly Phe Ser Pro Tyr Tyr Phe Pro Tyr Trp
            100                 105                 110

Gly Gln Gly Ile Pro Val Ser Val Ser Ser
        115                 120
```

<210> SEQ ID NO 15
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION:

<400> SEQUENCE: 15

-continued

```
cag gtg aaa ctg ctc gag tct ggg gga ggc gtg gtc cac cct ggg agg        48
Gln Val Lys Leu Leu Glu Ser Gly Gly Gly Val Val His Pro Gly Arg
1               5                   10                  15 tcc ctg aga ctc tcc tgt gca gcc tct gga ttc acc ttc agt agc tat        96
Ser Leu Arg Leu Ser Cys Ala Ala Ser Gly Phe Thr Phe Ser Ser Tyr
            20                  25                  30 act atg cac tgg gtc cgc cag gct cca ggc aag ggg ctg gag tgg gtg       144
Thr Met His Trp Val Arg Gln Ala Pro Gly Lys Gly Leu Glu Trp Val
        35                  40                  45 gca ctt ata tca tat gat gga agc aat aaa tac tac gca gac tcc gtg       192
Ala Leu Ile Ser Tyr Asp Gly Ser Asn Lys Tyr Tyr Ala Asp Ser Val
50                  55                  60 aag ggc cga ttc gcc atc tcc aga gac aat tcc aag aac acg cta tat       240
Lys Gly Arg Phe Ala Ile Ser Arg Asp Asn Ser Lys Asn Thr Leu Tyr
65                  70                  75                  80 ctg caa atg aac agc ctg aga gct gag gac acg gct gtg tat tac tgt       288
Leu Gln Met Asn Ser Leu Arg Ala Glu Asp Thr Ala Val Tyr Tyr Cys
                85                  90                  95 gcg aaa gat ggc cgg agt ggg agc tac gcc agg ttc gac ggt atg gac       336
Ala Lys Asp Gly Arg Ser Gly Ser Tyr Ala Arg Phe Asp Gly Met Asp
            100                 105                 110 gtc tgg ggc caa ggg acc acg gtc acc gtc tcc tca                       372
Val Trp Gly Gln Gly Thr Thr Val Thr Val Ser Ser
        115                 120
```

<210> SEQ ID NO 16
<211> LENGTH: 124
<212> TYPE: PRT
<213> ORGANISM: Homo sapiens

<400> SEQUENCE: 16

```
Gln Val Lys Leu Leu Glu Ser Gly Gly Gly Val Val His Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Ala Leu Ile Ser Tyr Asp Gly Ser Asn Lys Tyr Tyr Ala Asp Ser Val
50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Arg Ser Gly Ser Tyr Ala Arg Phe Asp Gly Met Asp
            100                 105                 110

Val Trp Gly Gln Gly Thr Thr Val Thr Val Ser Ser
        115                 120
```

<210> SEQ ID NO 17
<211> LENGTH: 372
<212> TYPE: DNA
<213> ORGANISM: Homo sapiens
<220> FEATURE:
<221> NAME/KEY: CDS
<222> LOCATION: (1)..(372)
<223> OTHER INFORMATION:

<400> SEQUENCE: 17

```
cag gtg aaa ctg ctc gag tct ggg gga ggc ttg gta cag cct ggc agg        48
Gln Val Lys Leu Leu Glu Ser Gly Gly Gly Leu Val Gln Pro Gly Arg
1               5                   10                  15
```

```
tcc ctg aga ctc tcc tgt gca gcc tct gga ttc acc ttt gat gat tat    96
Ser Leu Arg Leu Ser Cys Ala Ala Ser Gly Phe Thr Phe Asp Asp Tyr
        20                  25                  30 gcc ctg cac tgg gtc cgt caa gct cca ggg aag ggc ctg gag tgg gtc   144
Ala Leu His Trp Val Arg Gln Ala Pro Gly Lys Gly Leu Glu Trp Val
            35                  40                  45 tca ggt att agt tgg gat agt ggt acc ata ggc tat gcg gac tct gtg   192
Ser Gly Ile Ser Trp Asp Ser Gly Thr Ile Gly Tyr Ala Asp Ser Val
 50                  55                  60 aag ggc cga ttc acc atc tcc aga gac aac gcc aag aac tcc ctg tat   240
Lys Gly Arg Phe Thr Ile Ser Arg Asp Asn Ala Lys Asn Ser Leu Tyr
 65                  70                  75                  80 ctg caa atg aac agt ctg aga gct gag gac acg gcc ttg tat tac tgt   288
Leu Gln Met Asn Ser Leu Arg Ala Glu Asp Thr Ala Leu Tyr Tyr Cys
                 85                  90                  95 gta aaa gat atg ggg tct tcg gta gtg gct acg tac aat gct ttt gat   336
Val Lys Asp Met Gly Ser Ser Val Val Ala Thr Tyr Asn Ala Phe Asp
            100                 105                 110 atc tgg ggc caa ggg aca atg gtc acc gtc tct tca                   372
Ile Trp Gly Gln Gly Thr Met Val Thr Val Ser Ser
        115                 120
```

<210> SEQ ID NO 18
<211> LENGTH: 124
<212> TYPE: PRT
<213> ORGANISM: Homo sapiens

<400> SEQUENCE: 18

```
Gln Val Lys Leu Leu Glu Ser Gly Gly Gly Leu Val Gln Pro Gly Arg
 1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Ile Ser Trp Asp Ser Gly Thr Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Val Lys Asp Met Gly Ser Ser Val Val Ala Thr Tyr Asn Ala Phe Asp
            100                 105                 110

Ile Trp Gly Gln Gly Thr Met Val Thr Val Ser Ser
        115                 120
```

<210> SEQ ID NO 19
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION:

<400> SEQUENCE: 19

```
cag gtg aaa ctg ctc gag tca ggc cca gga ctg gtg aag cct tcg gag    48
Gln Val Lys Leu Leu Glu Ser Gly Pro Gly Leu Val Lys Pro Ser Glu
 1               5                   10                  15 acc ctg tcc ctc acc tgc act gtc tct ggt ggc tcc ttc agt act tac    96
Thr Leu Ser Leu Thr Cys Thr Val Ser Gly Gly Ser Phe Ser Thr Tyr
```

```
                  20                  25                  30
tat tgg agc tgg atc cgg cag ccc cca ggg aag gga ctg gag tgg att      144
Tyr Trp Ser Trp Ile Arg Gln Pro Pro Gly Lys Gly Leu Glu Trp Ile
         35                  40                  45 ggg tat atc tat tac agt ggg aac acc aac tac aac ccc tcc ctc aag      192
Gly Tyr Ile Tyr Tyr Ser Gly Asn Thr Asn Tyr Asn Pro Ser Leu Lys
 50                  55                  60 agt cga gcc acc ata tca gta gac acg tcc aag aac cag ttc tcc ctg      240
Ser Arg Ala Thr Ile Ser Val Asp Thr Ser Lys Asn Gln Phe Ser Leu
65                  70                  75                  80 aag ctg agc tct gtt acc gcc gca gac acg gcc gta tat tac tgt gcg      288
Lys Leu Ser Ser Val Thr Ala Ala Asp Thr Ala Val Tyr Tyr Cys Ala
                 85                  90                  95 aga ctg cgt aac gat ggc tgg aat gat ggc ttt gat atc tgg ggc caa      336
Arg Leu Arg Asn Asp Gly Trp Asn Asp Gly Phe Asp Ile Trp Gly Gln
            100                 105                 110 ggg aca atg gtc acc gtc tct tca                                      360
Gly Thr Met Val Thr Val Ser Ser
        115                 120

<210> SEQ ID NO 20
<211> LENGTH: 120
<212> TYPE: PRT
<213> ORGANISM: Homo sapiens

<400> SEQUENCE: 20

Gln Val Lys Leu Leu Glu Ser Gly Pro Gly Leu Val Lys Pro Ser Glu
1               5                   10                  15

Thr Leu Ser Leu Thr Cys Thr Val Ser Gly Gly Ser Phe Ser Thr Tyr
            20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Asn Thr Asn Tyr Asn Pro Ser Leu Lys
 50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                 85                  90                  95

Arg Leu Arg Asn Asp Gly Trp Asn Asp Gly Phe Asp Ile Trp Gly Gln
            100                 105                 110

Gly Thr Met Val Thr Val Ser Ser
        115                 120

<210> SEQ ID NO 21
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION:

<400> SEQUENCE: 21 cag gtg aaa ctg ctc gag tct ggg gga ggc gtg gtc cag cct ggg agg       48
Gln Val Lys Leu Leu Glu Ser Gly Gly Gly Val Val Gln Pro Gly Arg
1               5                   10                  15 tcc ctg aga ctc tcc tgt gca gcc tct gga ttc acc ttc agt gac tat       96
Ser Leu Arg Leu Ser Cys Ala Ala Ser Gly Phe Thr Phe Ser Asp Tyr
            20                  25                  30 ggc atg cac tgg gtc cgc cag gct cca ggc aag ggg ctg gag tgg gtg      144
```

```
Gly Met His Trp Val Arg Gln Ala Pro Gly Lys Gly Leu Glu Trp Val
        35                  40                  45 gca gct ata tca tat gat gga agt aac aaa tac tat gca gac tcc gtg      192
Ala Ala Ile Ser Tyr Asp Gly Ser Asn Lys Tyr Tyr Ala Asp Ser Val
 50                  55                  60 aag ggc cga ttc tcc atc tcc aga gac aat tcc aac aat acg cta tat      240
Lys Gly Arg Phe Ser Ile Ser Arg Asp Asn Ser Asn Asn Thr Leu Tyr
 65              70                  75                  80 ctg caa atg agc acc ctg aga gct gag gac acg gct gtc tat ttc tgt      288
Leu Gln Met Ser Thr Leu Arg Ala Glu Asp Thr Ala Val Tyr Phe Cys
                 85                  90                  95 gcg aga gat tcg gaa acg gca ata gcg gca gct gga cgg ttt gat atc      336
Ala Arg Asp Ser Glu Thr Ala Ile Ala Ala Ala Gly Arg Phe Asp Ile
                100                 105                 110 tgg ggc caa ggg aca atg gtc acc gtc tct tca                          369
Trp Gly Gln Gly Thr Met Val Thr Val Ser Ser
        115                 120
```

<210> SEQ ID NO 22
<211> LENGTH: 123
<212> TYPE: PRT
<213> ORGANISM: Homo sapiens

<400> SEQUENCE: 22

```
Gln Val Lys Leu Leu Glu Ser Gly Gly Val Val Gln Pro Gly Arg
 1               5                   10                  15

Ser Leu Arg Leu Ser Cys Ala Ala Ser Gly Phe Thr Phe Ser Asp Tyr
                 20                  25                  30

Gly Met His Trp Val Arg Gln Ala Pro Gly Lys Gly Leu Glu Trp Val
            35                  40                  45

Ala Ala Ile Ser Tyr Asp Gly Ser Asn Lys Tyr Tyr Ala Asp Ser Val
 50                  55                  60

Lys Gly Arg Phe Ser Ile Ser Arg Asp Asn Ser Asn Asn Thr Leu Tyr
 65              70                  75                  80

Leu Gln Met Ser Thr Leu Arg Ala Glu Asp Thr Ala Val Tyr Phe Cys
                 85                  90                  95

Ala Arg Asp Ser Glu Thr Ala Ile Ala Ala Ala Gly Arg Phe Asp Ile
                100                 105                 110

Trp Gly Gln Gly Thr Met Val Thr Val Ser Ser
            115                 120
```

<210> SEQ ID NO 23
<211> LENGTH: 366
<212> TYPE: DNA
<213> ORGANISM: Homo sapiens
<220> FEATURE:
<221> NAME/KEY: CDS
<222> LOCATION: (1)..(366)
<223> OTHER INFORMATION:

<400> SEQUENCE: 23

```
cag gtg aaa ctg ctc gag tct ggg gct gag gtg aag aag cct ggg tcc      48
Gln Val Lys Leu Leu Glu Ser Gly Ala Glu Val Lys Lys Pro Gly Ser
 1               5                   10                  15 tcg gtg atg gtc tcc tgc aag gct tct gga ggc acc ttc agc agc cat      96
Ser Val Met Val Ser Cys Lys Ala Ser Gly Gly Thr Phe Ser Ser His
                 20                  25                  30 act atc agc tgg gtg cgg cag gcc cct gga caa ggc ctt gag tgg atg     144
Thr Ile Ser Trp Val Arg Gln Ala Pro Gly Gln Gly Leu Glu Trp Met
            35                  40                  45
```

```
gga ggg atc acc cct atc ttt ggt aca gtg aac tac gca cag aag ttc        192
Gly Gly Ile Thr Pro Ile Phe Gly Thr Val Asn Tyr Ala Gln Lys Phe
 50                  55                  60 cag ggc aga gtc acc att acc gcg gac gaa ccc acg agc aca gcc tac        240
Gln Gly Arg Val Thr Ile Thr Ala Asp Glu Pro Thr Ser Thr Ala Tyr
 65                  70                  75                  80 atg gaa ctg agg agc ctg aca tct gac gac tcg ggc atc tat tac tgt        288
Met Glu Leu Arg Ser Leu Thr Ser Asp Asp Ser Gly Ile Tyr Tyr Cys
                 85                  90                  95 gcg aga gaa gat ggc act aca gta cca agt caa ccc ctt gag ttc tgg        336
Ala Arg Glu Asp Gly Thr Thr Val Pro Ser Gln Pro Leu Glu Phe Trp
            100                 105                 110 ggc cag gga acc cgg gtc acc gtc tcc tct                                366
Gly Gln Gly Thr Arg Val Thr Val Ser Ser
        115                 120

<210> SEQ ID NO 24
<211> LENGTH: 122
<212> TYPE: PRT
<213> ORGANISM: Homo sapiens

<400> SEQUENCE: 24

Gln Val Lys Leu Leu Glu Ser Gly Ala Glu Val Lys Lys Pro Gly Ser
 1               5                  10                  15

Ser Val Met Val Ser Cys Lys Ala Ser Gly Gly Thr Phe Ser Ser His
                 20                  25                  30

Thr Ile Ser Trp Val Arg Gln Ala Pro Gly Gln Gly Leu Glu Trp Met
             35                  40                  45

Gly Gly Ile Thr Pro Ile Phe Gly Thr Val Asn Tyr Ala Gln Lys Phe
 50                  55                  60

Gln Gly Arg Val Thr Ile Thr Ala Asp Glu Pro Thr Ser Thr Ala Tyr
 65                  70                  75                  80

Met Glu Leu Arg Ser Leu Thr Ser Asp Asp Ser Gly Ile Tyr Tyr Cys
                 85                  90                  95

Ala Arg Glu Asp Gly Thr Thr Val Pro Ser Gln Pro Leu Glu Phe Trp
            100                 105                 110

Gly Gln Gly Thr Arg Val Thr Val Ser Ser
        115                 120

<210> SEQ ID NO 25
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION:

<400> SEQUENCE: 25 cag gtg aaa ctg ctc gag tct ggg gga ggc ttg gtc cag cct ggg ggg        48
Gln Val Lys Leu Leu Glu Ser Gly Gly Gly Leu Val Gln Pro Gly Gly
 1               5                  10                  15 tcc ctg aga ctc tcc tgt tca gcc tct gga ttc acc ttc aat aaa tat       96
Ser Leu Arg Leu Ser Cys Ser Ala Ser Gly Phe Thr Phe Asn Lys Tyr
                 20                  25                  30 gca ata cac tgg gtc cgc cag gct cca ggg aag gga ctg gaa tat gtt      144
Ala Ile His Trp Val Arg Gln Ala Pro Gly Lys Gly Leu Glu Tyr Val
             35                  40                  45 tca gct att agt agt aat ggg ggt aac aca tac tac gca gac tcc gtg      192
Ser Ala Ile Ser Ser Asn Gly Gly Asn Thr Tyr Tyr Ala Asp Ser Val
 50                  55                  60
```

```
aag ggc aga ttc acc atc tcc aga gac aat tcc aag aac acg gtg tat      240
Lys Gly Arg Phe Thr Ile Ser Arg Asp Asn Ser Lys Asn Thr Val Tyr
 65                  70                  75                  80 ctt caa atg agc agt ctg aga gct gag gac acg gct gtg tat tac tgt      288
Leu Gln Met Ser Ser Leu Arg Ala Glu Asp Thr Ala Val Tyr Tyr Cys
                 85                  90                  95 gtt aga gga agt ggg agc tac tta gga tac tac ttt gac tac tgg ggc      336
Val Arg Gly Ser Gly Ser Tyr Leu Gly Tyr Tyr Phe Asp Tyr Trp Gly
            100                 105                 110 cag gga acc ctg gtc acc gtc tcc tca                                  363
Gln Gly Thr Leu Val Thr Val Ser Ser
        115                 120

<210> SEQ ID NO 26
<211> LENGTH: 121
<212> TYPE: PRT
<213> ORGANISM: Homo sapiens

<400> SEQUENCE: 26

Gln Val Lys Leu Leu Glu Ser Gly Gly Gly Leu Val Gln Pro Gly Gly
 1               5                  10                  15

Ser Leu Arg Leu Ser Cys Ser Ala Ser Gly Phe Thr Phe Asn Lys Tyr
            20                  25                  30

Ala Ile His Trp Val Arg Gln Ala Pro Gly Lys Gly Leu Glu Tyr Val
        35                  40                  45

Ser Ala Ile Ser Ser Asn Gly Gly Asn Thr Tyr Tyr Ala Asp Ser Val
    50                  55                  60

Lys Gly Arg Phe Thr Ile Ser Arg Asp Asn Ser Lys Asn Thr Val Tyr
 65                  70                  75                  80

Leu Gln Met Ser Ser Leu Arg Ala Glu Asp Thr Ala Val Tyr Tyr Cys
                 85                  90                  95

Val Arg Gly Ser Gly Ser Tyr Leu Gly Tyr Tyr Phe Asp Tyr Trp Gly
            100                 105                 110

Gln Gly Thr Leu Val Thr Val Ser Ser
        115                 120

<210> SEQ ID NO 27
<211> LENGTH: 366
<212> TYPE: DNA
<213> ORGANISM: Homo sapiens
<220> FEATURE:
<221> NAME/KEY: CDS
<222> LOCATION: (1)..(366)
<223> OTHER INFORMATION:

<400> SEQUENCE: 27 gtg gtg act cag cca ccc tcg gtg tca gtg gct cca aga cag acg gcc       48
Val Val Thr Gln Pro Pro Ser Val Ser Val Ala Pro Arg Gln Thr Ala
 1               5                  10                  15 acg att acc tgt ggg gga tac aag att gga agt aaa agt gtc cac tgg       96
Thr Ile Thr Cys Gly Gly Tyr Lys Ile Gly Ser Lys Ser Val His Trp
            20                  25                  30 tac caa cag aag cca ggc cag gcc cct gta ttg gtc gtc tat gag gat      144
Tyr Gln Gln Lys Pro Gly Gln Ala Pro Val Leu Val Val Tyr Glu Asp
        35                  40                  45 tcc tac cgg ccc tca gag atc cct gag cga ttc tct ggc tcc aac tct      192
Ser Tyr Arg Pro Ser Glu Ile Pro Glu Arg Phe Ser Gly Ser Asn Ser
    50                  55                  60 ggg aac atg gcc acc ctg acc atc acc ggg gtc gaa gcc ggg gat gag      240
Gly Asn Met Ala Thr Leu Thr Ile Thr Gly Val Glu Ala Gly Asp Glu
```

```
                                 65                  70                  75                  80
gcc gac tac tac tgt cag gtg tgg gat aat act aat gat cag acg ata      288
Ala Asp Tyr Tyr Cys Gln Val Trp Asp Asn Thr Asn Asp Gln Thr Ile
                        85                  90                  95 ttc ggc gga ggg acc aag ctg acc gtc cta cgt cag ccc aag gct gcc      336
Phe Gly Gly Gly Thr Lys Leu Thr Val Leu Arg Gln Pro Lys Ala Ala
            100                 105                 110 ccc tcg gtc act ctg ttc ccg ccc tcc tct                              366
Pro Ser Val Thr Leu Phe Pro Pro Ser Ser
        115                 120

<210> SEQ ID NO 28
<211> LENGTH: 122
<212> TYPE: PRT
<213> ORGANISM: Homo sapiens

<400> SEQUENCE: 28

Val Val Thr Gln Pro Pro Ser Val Ser Val Ala Pro Arg Gln Thr Ala
 1               5                  10                  15

Thr Ile Thr Cys Gly Gly Tyr Lys Ile Gly Ser Lys Ser Val His Trp
            20                  25                  30

Tyr Gln Gln Lys Pro Gly Gln Ala Pro Val Leu Val Val Tyr Glu Asp
        35                  40                  45

Ser Tyr Arg Pro Ser Glu Ile Pro Glu Arg Phe Ser Gly Ser Asn Ser
    50                  55                  60

Gly Asn Met Ala Thr Leu Thr Ile Thr Gly Val Glu Ala Gly Asp Glu
65                  70                  75                  80

Ala Asp Tyr Tyr Cys Gln Val Trp Asp Asn Thr Asn Asp Gln Thr Ile
                85                  90                  95

Phe Gly Gly Gly Thr Lys Leu Thr Val Leu Arg Gln Pro Lys Ala Ala
            100                 105                 110

Pro Ser Val Thr Leu Phe Pro Pro Ser Ser
        115                 120

<210> SEQ ID NO 29
<211> LENGTH: 366
<212> TYPE: DNA
<213> ORGANISM: Homo sapiens
<220> FEATURE:
<221> NAME/KEY: CDS
<222> LOCATION: (1)..(366)
<223> OTHER INFORMATION:

<400> SEQUENCE: 29 cag gtg aaa ctg ctc gag tct ggg gct gag gtg aag aag cct ggg gcc      48
Gln Val Lys Leu Leu Glu Ser Gly Ala Glu Val Lys Lys Pro Gly Ala
 1               5                  10                  15 tca gtg aag gtc tcc tgc aag gtt tcc gga tac acc ctc act gaa tta      96
Ser Val Lys Val Ser Cys Lys Val Ser Gly Tyr Thr Leu Thr Glu Leu
            20                  25                  30 tcc atg cac tgg gtg cga cag gct cct gga aaa ggg ctt gag tgg atg     144
Ser Met His Trp Val Arg Gln Ala Pro Gly Lys Gly Leu Glu Trp Met
        35                  40                  45 gga ggt ttt gat cct gaa gat ggt gaa aca atc tac gca cag aaa ttc     192
Gly Gly Phe Asp Pro Glu Asp Gly Glu Thr Ile Tyr Ala Gln Lys Phe
    50                  55                  60 cag ggc aga gtc acc atg acc gag gac aca tct aca gac acg gcc tac     240
Gln Gly Arg Val Thr Met Thr Glu Asp Thr Ser Thr Asp Thr Ala Tyr
65                  70                  75                  80 atg gag ctg agc agc ctg aga tct gag gac acg gcc gtg tat tac tgt     288
```

```
                 Met Glu Leu Ser Ser Leu Arg Ser Glu Asp Thr Ala Val Tyr Tyr Cys
                                  85                  90                  95 gag aca ggt ctg agg tcg tac aac tat ggt cgt aac ctt gac tat tgg                  336
Glu Thr Gly Leu Arg Ser Tyr Asn Tyr Gly Arg Asn Leu Asp Tyr Trp
            100                 105                 110 ggc cag gga acc ctg gtc acc gtc tcc tca                                           366
Gly Gln Gly Thr Leu Val Thr Val Ser Ser
        115                 120
```

<210> SEQ ID NO 30
<211> LENGTH: 122
<212> TYPE: PRT
<213> ORGANISM: Homo sapiens

<400> SEQUENCE: 30

```
Gln Val Lys Leu Leu Glu Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Glu Thr Gly Leu Arg Ser Tyr Asn Tyr Gly Arg Asn Leu Asp Tyr Trp
            100                 105                 110

Gly Gln Gly Thr Leu Val Thr Val Ser Ser
        115                 120
```

<210> SEQ ID NO 31
<211> LENGTH: 11
<212> TYPE: PRT
<213> ORGANISM: Homo sapiens

<400> SEQUENCE: 31

```
Val Leu Pro Phe Asp Pro Ile Ser Met Asp Val
1               5                   10
```

<210> SEQ ID NO 32
<211> LENGTH: 14
<212> TYPE: PRT
<213> ORGANISM: Homo sapiens

<400> SEQUENCE: 32

```
Ala Leu Gly Ser Trp Gly Gly Trp Asp His Tyr Met Asp Val
1               5                   10
```

<210> SEQ ID NO 33
<211> LENGTH: 5
<212> TYPE: PRT
<213> ORGANISM: Homo sapiens

<400> SEQUENCE: 33

```
Gly Tyr Ser Trp Arg
1               5
```

<210> SEQ ID NO 34
<211> LENGTH: 5

```
<212> TYPE: PRT
<213> ORGANISM: Homo sapiens

<400> SEQUENCE: 34

Ser Tyr Ala Met His
1               5

<210> SEQ ID NO 35
<211> LENGTH: 16
<212> TYPE: PRT
<213> ORGANISM: Homo sapiens

<400> SEQUENCE: 35

Asp Ile Ser Tyr Ser Gly Ser Thr Lys Tyr Lys Pro Ser Leu Arg Ser
1               5                   10                  15

<210> SEQ ID NO 36
<211> LENGTH: 17
<212> TYPE: PRT
<213> ORGANISM: Homo sapiens

<400> SEQUENCE: 36

Val Ile Ser Tyr Asp Gly Ser Asn Lys Tyr Tyr Ala Asp Ser Val Lys
1               5                   10                  15

Gly

<210> SEQ ID NO 37
<211> LENGTH: 11
<212> TYPE: PRT
<213> ORGANISM: Homo sapiens

<400> SEQUENCE: 37

Ala Thr Trp Asp Asp Gly Leu Asn Gly Pro Val
1               5                   10

<210> SEQ ID NO 38
<211> LENGTH: 11
<212> TYPE: PRT
<213> ORGANISM: Homo sapiens

<400> SEQUENCE: 38

Ala Ala Trp Asp Asp Ser Leu Asn Gly Trp Val
1               5                   10

<210> SEQ ID NO 39
<211> LENGTH: 13
<212> TYPE: PRT
<213> ORGANISM: Homo sapiens

<400> SEQUENCE: 39

Ser Gly Ser Ser Ser Asn Ile Arg Ser Asn Pro Val Ser
1               5                   10

<210> SEQ ID NO 40
<211> LENGTH: 13
<212> TYPE: PRT
<213> ORGANISM: Homo sapiens

<400> SEQUENCE: 40

Ser Gly Ser Ser Ser Asn Ile Gly Ser Asn Thr Val Asn
1               5                   10

<210> SEQ ID NO 41
<211> LENGTH: 7
```

-continued

<212> TYPE: PRT
<213> ORGANISM: Homo sapiens

<400> SEQUENCE: 41

Gly Ser His Gln Arg Pro Ser
1               5

<210> SEQ ID NO 42
<211> LENGTH: 7
<212> TYPE: PRT
<213> ORGANISM: Homo sapiens

<400> SEQUENCE: 42

Ser Asn Asn Gln Arg Pro Ser
1               5

<210> SEQ ID NO 43
<211> LENGTH: 16
<212> TYPE: PRT
<213> ORGANISM: Homo sapiens

<400> SEQUENCE: 43

Val Arg Asp Leu Gly Tyr Arg Val Leu Ser Thr Phe Thr Phe Asp Ile
1               5                   10                  15

<210> SEQ ID NO 44
<211> LENGTH: 15
<212> TYPE: PRT
<213> ORGANISM: Homo sapiens

<400> SEQUENCE: 44

Asp Gly Arg Ser Gly Ser Tyr Ala Arg Phe Asp Gly Met Asp Val
1               5                   10                  15

<210> SEQ ID NO 45
<211> LENGTH: 14
<212> TYPE: PRT
<213> ORGANISM: Homo sapiens

<400> SEQUENCE: 45

Met Gly Ser Ser Val Val Ala Thr Tyr Asn Ala Phe Asp Ile
1               5                   10

<210> SEQ ID NO 46
<211> LENGTH: 14
<212> TYPE: PRT
<213> ORGANISM: Homo sapiens

<400> SEQUENCE: 46

Asp Ala Asp Gly Asp Gly Phe Ser Pro Tyr Tyr Phe Pro Tyr
1               5                   10

<210> SEQ ID NO 47
<211> LENGTH: 12
<212> TYPE: PRT
<213> ORGANISM: Homo sapiens

<400> SEQUENCE: 47

Leu Arg Asn Asp Gly Trp Asn Asp Gly Phe Asp Ile
1               5                   10

<210> SEQ ID NO 48
<211> LENGTH: 14
<212> TYPE: PRT
<213> ORGANISM: Homo sapiens

<400> SEQUENCE: 48

Asp Ser Glu Thr Ala Ile Ala Ala Ala Gly Arg Phe Asp Ile
1               5                   10

<210> SEQ ID NO 49
<211> LENGTH: 13
<212> TYPE: PRT
<213> ORGANISM: Homo sapiens

<400> SEQUENCE: 49

Glu Asp Gly Thr Thr Val Pro Ser Gln Pro Leu Glu Phe
1               5                   10

<210> SEQ ID NO 50
<211> LENGTH: 12
<212> TYPE: PRT
<213> ORGANISM: Homo sapiens

<400> SEQUENCE: 50

Gly Ser Gly Ser Tyr Leu Gly Tyr Tyr Phe Asp Tyr
1               5                   10

<210> SEQ ID NO 51
<211> LENGTH: 13
<212> TYPE: PRT
<213> ORGANISM: Homo sapiens

<400> SEQUENCE: 51

Gly Leu Arg Ser Tyr Asn Tyr Gly Arg Asn Leu Asp Tyr
1               5                   10

<210> SEQ ID NO 52
<211> LENGTH: 9
<212> TYPE: PRT
<213> ORGANISM: Homo sapiens

<400> SEQUENCE: 52

Cys Ser Tyr Val His Ser Ser Thr Asn
1               5

<210> SEQ ID NO 53
<211> LENGTH: 9
<212> TYPE: PRT
<213> ORGANISM: Homo sapiens

<400> SEQUENCE: 53

Gln Val Trp Asp Asn Thr Asn Asp Gln
1               5

<210> SEQ ID NO 54
<211> LENGTH: 5
<212> TYPE: PRT
<213> ORGANISM: Homo sapiens

<400> SEQUENCE: 54

Asn Phe Ala Met Ser
1               5

<210> SEQ ID NO 55
<211> LENGTH: 5
<212> TYPE: PRT
<213> ORGANISM: Homo sapiens

<400> SEQUENCE: 55

Ser Tyr Thr Met His
1               5

<210> SEQ ID NO 56
<211> LENGTH: 5
<212> TYPE: PRT
<213> ORGANISM: Homo sapiens

<400> SEQUENCE: 56

Asp Tyr Ala Leu His
1               5

<210> SEQ ID NO 57
<211> LENGTH: 5
<212> TYPE: PRT
<213> ORGANISM: Homo sapiens

<400> SEQUENCE: 57

Ser His Tyr Trp Ser
1               5

<210> SEQ ID NO 58
<211> LENGTH: 5
<212> TYPE: PRT
<213> ORGANISM: Homo sapiens

<400> SEQUENCE: 58

Thr Tyr Tyr Trp Ser
1               5

<210> SEQ ID NO 59
<211> LENGTH: 5
<212> TYPE: PRT
<213> ORGANISM: Homo sapiens

<400> SEQUENCE: 59

Asp Tyr Gly Met His
1               5

<210> SEQ ID NO 60
<211> LENGTH: 5
<212> TYPE: PRT
<213> ORGANISM: Homo sapiens

<400> SEQUENCE: 60

Ser His Thr Ile Ser
1               5

<210> SEQ ID NO 61
<211> LENGTH: 5
<212> TYPE: PRT
<213> ORGANISM: Homo sapiens

<400> SEQUENCE: 61

Lys Tyr Ala Ile His
1               5

<210> SEQ ID NO 62
<211> LENGTH: 5
<212> TYPE: PRT
<213> ORGANISM: Homo sapiens

<400> SEQUENCE: 62

Glu Leu Ser Met His

```
1               5

<210> SEQ ID NO 63
<211> LENGTH: 17
<212> TYPE: PRT
<213> ORGANISM: Homo sapiens

<400> SEQUENCE: 63

Gly Ile Ser Gly Gly Gly Leu Leu Thr His Tyr Ala Asp Ser Val Lys
1               5                   10                  15

Gly

<210> SEQ ID NO 64
<211> LENGTH: 17
<212> TYPE: PRT
<213> ORGANISM: Homo sapiens

<400> SEQUENCE: 64

Gly Ile Ser Gly Gly Gly Leu Leu Thr His Tyr Ala Asn Ser Val Lys
1               5                   10                  15

Gly

<210> SEQ ID NO 65
<211> LENGTH: 17
<212> TYPE: PRT
<213> ORGANISM: Homo sapiens

<400> SEQUENCE: 65

Gly Ile Thr Pro Ile Phe Gly Thr Val Asn Tyr Ala Gln Lys Phe Gln
1               5                   10                  15

Gly

<210> SEQ ID NO 66
<211> LENGTH: 14
<212> TYPE: PRT
<213> ORGANISM: Homo sapiens

<400> SEQUENCE: 66

Thr Gly Thr Ser Ser Ala Ile Gly Asn Tyr Asn Phe Val Pro
1               5                   10

<210> SEQ ID NO 67
<211> LENGTH: 11
<212> TYPE: PRT
<213> ORGANISM: Homo sapiens

<400> SEQUENCE: 67

Gly Gly Tyr Lys Ile Gly Ser Lys Ser Val His
1               5                   10

<210> SEQ ID NO 68
<211> LENGTH: 7
<212> TYPE: PRT
<213> ORGANISM: Homo sapiens

<400> SEQUENCE: 68

Glu Gly Ser Lys Arg Pro Ser
1               5

<210> SEQ ID NO 69
<211> LENGTH: 7
<212> TYPE: PRT
<213> ORGANISM: Homo sapiens
```

```
<400> SEQUENCE: 69

Glu Asp Ser Tyr Arg Pro Ser
1               5

<210> SEQ ID NO 70
<211> LENGTH: 17
<212> TYPE: PRT
<213> ORGANISM: Homo sapiens

<400> SEQUENCE: 70

Gly Ile Ser Trp Asp Ser Thr Ser Ile Gly Tyr Ala Asp Ser Val Lys
1               5                   10                  15

Gly

<210> SEQ ID NO 71
<211> LENGTH: 16
<212> TYPE: PRT
<213> ORGANISM: Homo sapiens

<400> SEQUENCE: 71

Phe Ile Tyr Asp Gly Ala Arg Thr Arg Phe Asn Pro Ser Leu Arg Ser
1               5                   10                  15

<210> SEQ ID NO 72
<211> LENGTH: 17
<212> TYPE: PRT
<213> ORGANISM: Homo sapiens

<400> SEQUENCE: 72

Ala Ile Ser Ser Asn Gly Gly Asn Thr Tyr Tyr Ala Asp Ser Val Lys
1               5                   10                  15

Gly

<210> SEQ ID NO 73
<211> LENGTH: 17
<212> TYPE: PRT
<213> ORGANISM: Homo sapiens

<400> SEQUENCE: 73

Gly Phe Asp Pro Glu Asp Gly Glu Thr Ile Tyr Ala Gln Lys Phe Gln
1               5                   10                  15

Gly

<210> SEQ ID NO 74
<211> LENGTH: 17
<212> TYPE: PRT
<213> ORGANISM: Homo sapiens

<400> SEQUENCE: 74

Gly Ile Ser Gly Gly Gly Leu Leu Thr His Tyr Ala Asp Ser Val Lys
1               5                   10                  15

Gly

<210> SEQ ID NO 75
<211> LENGTH: 30
<212> TYPE: PRT
<213> ORGANISM: Homo sapiens

<400> SEQUENCE: 75

Arg Phe Thr Ile Ser Arg Asn Asn Ser Arg Asn Thr Val Tyr Leu Gln
1               5                   10                  15
```

Met Asn Ser Leu Arg Ala Glu Asp Thr Ala Val Tyr Tyr Cys
            20                  25                  30

<210> SEQ ID NO 76
<211> LENGTH: 17
<212> TYPE: PRT
<213> ORGANISM: Homo sapiens

<400> SEQUENCE: 76

Ala Ile Ser Gly Ser Gly Gly Ser Thr Tyr Tyr Ala Asn Ser Val Lys
1               5                   10                  15

Gly

<210> SEQ ID NO 77
<211> LENGTH: 17
<212> TYPE: PRT
<213> ORGANISM: Homo sapiens

<400> SEQUENCE: 77

Leu Ile Ser Tyr Asp Gly Ser Asn Lys Tyr Tyr Ala Asp Ser Val Lys
1               5                   10                  15

Gly

<210> SEQ ID NO 78
<211> LENGTH: 17
<212> TYPE: PRT
<213> ORGANISM: Homo sapiens

<400> SEQUENCE: 78

Gly Ile Ser Trp Asp Ser Thr Ser Ile Gly Tyr Ala Asp Ser Val Lys
1               5                   10                  15

Gly

<210> SEQ ID NO 79
<211> LENGTH: 16
<212> TYPE: PRT
<213> ORGANISM: Homo sapiens

<400> SEQUENCE: 79

Phe Ile Tyr Asp Gly Ala Arg Thr Arg Phe Asn Pro Ser Leu Arg Ser
1               5                   10                  15

<210> SEQ ID NO 80
<211> LENGTH: 14
<212> TYPE: PRT
<213> ORGANISM: Homo sapiens

<400> SEQUENCE: 80

Thr Gly Thr Ser Ser Ala Ile Gly Asn Tyr Asn Phe Val Pro
1               5                   10

<210> SEQ ID NO 81
<211> LENGTH: 7
<212> TYPE: PRT
<213> ORGANISM: Homo sapiens

<400> SEQUENCE: 81

Glu Gly Ser Lys Arg Pro Ser
1               5

<210> SEQ ID NO 82
<211> LENGTH: 9

<212> TYPE: PRT
<213> ORGANISM: Homo sapiens

<400> SEQUENCE: 82

Cys Ser Tyr Val His Ser Ser Thr Asn
1               5

<210> SEQ ID NO 83
<211> LENGTH: 5
<212> TYPE: PRT
<213> ORGANISM: Homo sapiens

<400> SEQUENCE: 83

Asp Tyr Gly Met His
1               5

<210> SEQ ID NO 84
<211> LENGTH: 17
<212> TYPE: PRT
<213> ORGANISM: Homo sapiens

<400> SEQUENCE: 84

Ala Ile Ser Tyr Asp Gly Ser Asn Lys Tyr Tyr Ala Asp Ser Val Lys
1               5                   10                  15
Gly

<210> SEQ ID NO 85
<211> LENGTH: 14
<212> TYPE: PRT
<213> ORGANISM: Homo sapiens

<400> SEQUENCE: 85

Asp Ser Glu Thr Ala Ile Ala Ala Ala Gly Arg Phe Asp Ile
1               5                   10

<210> SEQ ID NO 86
<211> LENGTH: 5
<212> TYPE: PRT
<213> ORGANISM: Homo sapiens

<400> SEQUENCE: 86

Ser His Thr Ile Ser
1               5

<210> SEQ ID NO 87
<211> LENGTH: 17
<212> TYPE: PRT
<213> ORGANISM: Homo sapiens

<400> SEQUENCE: 87

Gly Ile Thr Pro Ile Phe Gly Thr Val Asn Tyr Ala Gln Lys Phe Gln
1               5                   10                  15
Gly

<210> SEQ ID NO 88
<211> LENGTH: 17
<212> TYPE: PRT
<213> ORGANISM: Homo sapiens

<400> SEQUENCE: 88

Ala Ile Ser Ser Asn Gly Gly Asn Thr Tyr Tyr Ala Asp Ser Val Lys
1               5                   10                  15
Gly

<210> SEQ ID NO 89
<211> LENGTH: 12
<212> TYPE: PRT
<213> ORGANISM: Homo sapiens

<400> SEQUENCE: 89

Gly Ser Gly Ser Tyr Leu Gly Tyr Tyr Phe Asp Tyr
1               5                   10

<210> SEQ ID NO 90
<211> LENGTH: 13
<212> TYPE: PRT
<213> ORGANISM: Homo sapiens

<400> SEQUENCE: 90

Gly Leu Arg Ser Tyr Asn Tyr Gly Arg Asn Leu Asp Tyr
1               5                   10

<210> SEQ ID NO 91
<211> LENGTH: 5
<212> TYPE: PRT
<213> ORGANISM: Homo sapiens

<400> SEQUENCE: 91

Ser Tyr Ala Met His
1               5

<210> SEQ ID NO 92
<211> LENGTH: 5
<212> TYPE: PRT
<213> ORGANISM: Homo sapiens

<400> SEQUENCE: 92

Ser Tyr Ala Ile Ser
1               5

<210> SEQ ID NO 93
<211> LENGTH: 5
<212> TYPE: PRT
<213> ORGANISM: Homo sapiens

<400> SEQUENCE: 93

Ser Tyr Gly Met His
1               5

<210> SEQ ID NO 94
<211> LENGTH: 5
<212> TYPE: PRT
<213> ORGANISM: Homo sapiens

<400> SEQUENCE: 94

Glu Leu Ser Met His
1               5

<210> SEQ ID NO 95
<211> LENGTH: 17
<212> TYPE: PRT
<213> ORGANISM: Homo sapiens

<400> SEQUENCE: 95

Val Ile Ser Tyr Asp Gly Ser Asn Lys Tyr Tyr Ala Asp Ser Val Lys
1               5                   10                  15

Gly

```
<210> SEQ ID NO 96
<211> LENGTH: 17
<212> TYPE: PRT
<213> ORGANISM: Homo sapiens

<400> SEQUENCE: 96

Gly Ile Ile Pro Ile Phe Gly Thr Ala Asn Tyr Ala Gln Lys Phe Gln
1               5                   10                  15
Gly

<210> SEQ ID NO 97
<211> LENGTH: 17
<212> TYPE: PRT
<213> ORGANISM: Homo sapiens

<400> SEQUENCE: 97

Val Ile Ser Tyr Asp Gly Ser Asn Lys Tyr Tyr Ala Asp Ser Val Lys
1               5                   10                  15
Gly

<210> SEQ ID NO 98
<211> LENGTH: 17
<212> TYPE: PRT
<213> ORGANISM: Homo sapiens

<400> SEQUENCE: 98

Gly Phe Asp Pro Glu Asp Gly Glu Thr Ile Tyr Ala Gln Lys Phe Gln
1               5                   10                  15
Gly

<210> SEQ ID NO 99
<211> LENGTH: 9
<212> TYPE: PRT
<213> ORGANISM: Homo sapiens

<400> SEQUENCE: 99

Gln Val Trp Asp Asn Thr Asn Asp Gln
1               5

<210> SEQ ID NO 100
<211> LENGTH: 11
<212> TYPE: PRT
<213> ORGANISM: Homo sapiens

<400> SEQUENCE: 100

Gly Gly Asn Asn Ile Gly Ser Lys Ser Val His
1               5                   10

<210> SEQ ID NO 101
<211> LENGTH: 7
<212> TYPE: PRT
<213> ORGANISM: Homo sapiens

<400> SEQUENCE: 101

Tyr Asp Ser Asp Arg Pro Ser
1               5

<210> SEQ ID NO 102
<211> LENGTH: 9
<212> TYPE: PRT
<213> ORGANISM: Homo sapiens
```

```
<400> SEQUENCE: 102

Gln Val Trp Asp Ser Ser Ser Asp His
1               5

<210> SEQ ID NO 103
<211> LENGTH: 5
<212> TYPE: PRT
<213> ORGANISM: Homo sapiens

<400> SEQUENCE: 103

Ser Tyr Ala Met Ser
1               5

<210> SEQ ID NO 104
<211> LENGTH: 5
<212> TYPE: PRT
<213> ORGANISM: Homo sapiens

<400> SEQUENCE: 104

Ser Tyr Gly Met His
1               5

<210> SEQ ID NO 105
<211> LENGTH: 5
<212> TYPE: PRT
<213> ORGANISM: Homo sapiens

<400> SEQUENCE: 105

Asp Tyr Ala Met His
1               5

<210> SEQ ID NO 106
<211> LENGTH: 5
<212> TYPE: PRT
<213> ORGANISM: Homo sapiens

<400> SEQUENCE: 106

Ser Tyr Tyr Trp Ser
1               5

<210> SEQ ID NO 107
<211> LENGTH: 17
<212> TYPE: PRT
<213> ORGANISM: Homo sapiens

<400> SEQUENCE: 107

Ala Ile Ser Gly Ser Gly Gly Ser Thr Tyr Tyr Ala Asp Ser Val Lys
1               5                   10                  15

Gly

<210> SEQ ID NO 108
<211> LENGTH: 17
<212> TYPE: PRT
<213> ORGANISM: Homo sapiens

<400> SEQUENCE: 108

Val Ile Ser Tyr Asp Gly Ser Asn Lys Tyr Tyr Ala Asp Ser Val Lys
1               5                   10                  15

Gly

<210> SEQ ID NO 109
<211> LENGTH: 17
<212> TYPE: PRT
```

-continued

<213> ORGANISM: Homo sapiens

<400> SEQUENCE: 109

Gly Ile Ser Trp Asn Ser Gly Ser Ile Gly Tyr Ala Asp Ser Val Lys
1               5                   10                  15

Gly

<210> SEQ ID NO 110
<211> LENGTH: 16
<212> TYPE: PRT
<213> ORGANISM: Homo sapiens

<400> SEQUENCE: 110

Tyr Ile Tyr Tyr Ser Gly Ser Thr Asn Tyr Asn Pro Ser Leu Lys Ser
1               5                   10                  15

<210> SEQ ID NO 111
<211> LENGTH: 17
<212> TYPE: PRT
<213> ORGANISM: Homo sapiens

<400> SEQUENCE: 111

Leu Ile Ser Tyr Asp Gly Ser Asn Lys Tyr Tyr Ala Asp Ser Val Lys
1               5                   10                  15

Gly

<210> SEQ ID NO 112
<211> LENGTH: 16
<212> TYPE: PRT
<213> ORGANISM: Homo sapiens

<400> SEQUENCE: 112

Tyr Ile Tyr Tyr Ser Gly Asn Thr Asn Tyr Asn Pro Ser Leu Lys Ser
1               5                   10                  15

<210> SEQ ID NO 113
<211> LENGTH: 17
<212> TYPE: PRT
<213> ORGANISM: Homo sapiens

<400> SEQUENCE: 113

Ala Ile Ser Tyr Asp Gly Ser Asn Lys Tyr Tyr Ala Asp Ser Val Lys
1               5                   10                  15

Gly

<210> SEQ ID NO 114
<211> LENGTH: 17
<212> TYPE: PRT
<213> ORGANISM: Homo sapiens

<400> SEQUENCE: 114

Gly Ile Ser Trp Asp Ser Gly Thr Ile Gly Tyr Ala Asp Ser Val Lys
1               5                   10                  15

Gly

<210> SEQ ID NO 115
<211> LENGTH: 11
<212> TYPE: PRT
<213> ORGANISM: Homo sapiens

<400> SEQUENCE: 115

Gly Gly Tyr Lys Ile Gly Ser Lys Ser Val His

-continued

<210> SEQ ID NO 116
<211> LENGTH: 7
<212> TYPE: PRT
<213> ORGANISM: Homo sapiens

<400> SEQUENCE: 116

Glu Asp Ser Tyr Arg Pro Ser
1               5

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 117
cgctgtgccc ccagaggt                                                    18

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 118
ggccgcaaat tctatttcaa gg                                               22

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 119
gagacacacc agtgtggc                                                    18

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 120
cacaacagag gcagttcc                                                    18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 121
ctaaactagc tagtctcc                                                    18

```
<210> SEQ ID NO 122
<211> LENGTH: 11
<212> TYPE: PRT
<213> ORGANISM: Homo sapiens

<400> SEQUENCE: 122

Gly Gly Tyr Lys Ile Gly Ser Lys Ser Val His
1               5                   10

<210> SEQ ID NO 123
<211> LENGTH: 124
<212> TYPE: PRT
<213> ORGANISM: Homo sapiens

<400> SEQUENCE: 123

Gln Val Lys Leu Leu Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Ile Ser Trp Asp Ser Thr Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Asp Met Gly Ser Ser Val Val Ala Thr Tyr Asn Ala Phe Asp
            100                 105                 110

Ile Trp Gly Gln Gly Thr Met Val Thr Val Ser Ser
        115                 120

<210> SEQ ID NO 124
<211> LENGTH: 14
<212> TYPE: PRT
<213> ORGANISM: Homo sapiens

<400> SEQUENCE: 124

Thr Gly Thr Ser Ser Asp Val Gly Ser Tyr Asn Leu Val Ser
1               5                   10

<210> SEQ ID NO 125
<211> LENGTH: 7
<212> TYPE: PRT
<213> ORGANISM: Homo sapiens

<400> SEQUENCE: 125

Glu Val Ser Lys Arg Pro Ser
1               5

<210> SEQ ID NO 126
<211> LENGTH: 9
<212> TYPE: PRT
<213> ORGANISM: Homo sapiens

<400> SEQUENCE: 126

Cys Ser Tyr Ala Gly Ser Ser Thr Phe
1               5

<210> SEQ ID NO 127
<211> LENGTH: 5
<212> TYPE: PRT
```

```
<213> ORGANISM: Homo sapiens

<400> SEQUENCE: 127

Lys Tyr Ala Ile His
1               5

<210> SEQ ID NO 128
<211> LENGTH: 7
<212> TYPE: PRT
<213> ORGANISM: Homo sapiens

<400> SEQUENCE: 128

Arg Asn Asn Gln Arg Pro Ser
1               5
```

ANTI-GPIIB/IIIA RECOMBINANT ANTIBODIES

Figure 1:
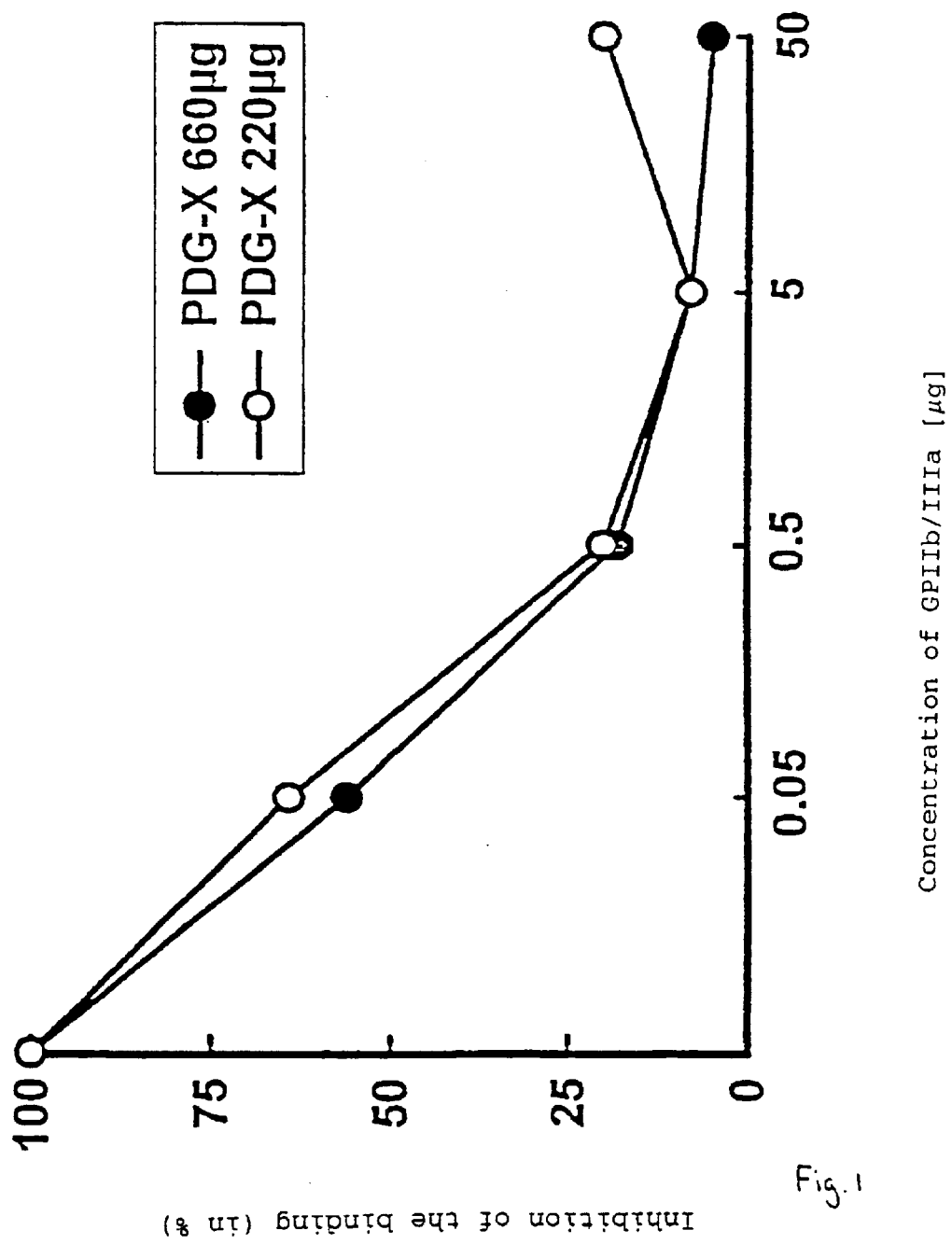

This application is the national phase of PCT/EP98/03397 filed on Jun. 5, 1998.

DESCRIPTION

The invention relates to novel nucleic acid sequences which encode human autoantibodies against blood platelet membrane proteins and which encode antiidiotypic antibodies, to novel amino acid sequences of human antibodies, and to their use for the diagnosis and therapy of diseases.

Autoimmune thrombocytopenic purpura (AITP) is an immune disease which is defined by a low blood platelet count associated with normal or elevated megakaryocytopoiesis. The destruction of platelets in the reticuloendothelial system (spleen, liver and bone marrow) is increased due to the presence of anti-platelet autoantibodies. These autoantibodies, which can be detected in about 75% of AITP patients, are predominantly directed against the platelet membrane glycoproteins (GP) IIb/IIIa and Ib/IX. Several different autoantibody specificities may be found in one and the same patient (cf., e.g., Berchtold and Wenger, Blood 81 (1993), 1246–1250; Kiefel et al., Br. J. Haematol. 79 (1991), 256–262; McMillan et al., Blood 70 (1987), 1040 and Fujisawa et al., Blood 79 (1991); 1441). However, it is still difficult to characterize binding epitopes and to ascertain the pathogenic significance of the autoantibodies due to the limited quantity of autoantibodies which can be obtained from AITP patients. It has only been possible to obtain a few human monoclonal antibodies from lymphocytes of AITP patients which react with GPIIb/IIIa AIPT using the hybridoma technique (Kunicki et al., Hum. Antibodies Hybridiomas 1(1990) 83–95).

Natural autoantibodies against various selfantigens, for example against intracellular and cytoskeletal components of human platelets, have also been reported to occur in healthy individuals (Guilbert et al., J. Immunol. 128 (1982), 2779–2787; Hurez et al., Eur. J. Immunol. 23 (1993), 783–789 and Pfueller et al., Clin. Exp. Immunol. 79 (1990), 367–373). Some of these autoantibodies which have been observed in sera from healthy individuals can also be directed against platelet-membrane proteins (Souberbielle, Eur. J. Haematol. 56 (1996), 178–180). However, the role of these natural autoantibodies, and there relationship to disease-associated autoantibodies, is still unknown.

Corticosteroids can be used for treating AITP. About half of the patients react within 4 weeks to an administration of prednisone; however long-term remissions are only rarely seen. The administration of high doses of intravenous immunoglobulin (IVIgG) is recommended as an emergency treatment for patients who are exhibiting severe bleeding or extremely low platelet counts. This treatment is followed in most patients by a rapid, but usually only transient, increase in the platelet count. The mechanisms by which corticosteroids and IVIgG act in the treatment of AITP are still unknown. Investigations carried out by Berchtold et al., (Blood 74 (1989), 2414–2417 and Berchtold and Wenger, Blood 81 (1993), 1246–1250) have disclosed that antiidiotypic antibodies which are present in IVIgG can inhibit the binding of autoantibodies to platelet glycoproteins.

The problem underlying the present application is that of identifying novel DNA sequences which are responsible for autoantibodies binding to GPIIb/IIIa. This approach can be used for making available novel pharmaceutical preparations which can be employed for improving the diagnosis and therapy of AITP.

It was surprisingly possible to identify binding sequences from autoantibodies after using peripheral circulating B cells from a healthy human donor to prepare a combinatorial phagemid display library of human antibody heavy and light chains. Following the presentation of human heavy and light antibody Fab fragments on the surface of the filamentous phage M13, it was possible to identify phage clones which exhibit specific binding to GPIIb/IIIa.

For this, the phagemid library was brought consecutively into contact with thrombasthenic platelets lacking GPIIb/IIIa (negative selection) and normal platelets (positive selection). After several rounds of selection and amplification by infecting $E.coli$, 23 clones were obtained which were able to bind to the GPIIb/IIIa complex. Inhibition studies using pools of monoclonal antibodies directed against the GPIIb/IIIa yielded two groups of clones: both groups were inhibited by monoclonal antibodies which were specific for the GPIIb/IIIa complex and one group was also inhibited by a GPIIb-specific monoclonal antibody. These findings were confirmed by carrying out a DNA analysis of the clones which indicated the presence of 2 different anti-GPIIb/IIIa phage clones. These results demonstrate that 2 GPIIb/IIIa-specific phage clones, i.e. autoantibodies, can be cloned from the genome of a healthy individual and that these clones are able to recognize confirmational epitopes belonging to the GPIIb/IIIa complex. Inhibition studies furthermore established that both phage clones inhibit the binding of platelet-associated autoantibodies from AITP patients to purified GPIIb/IIIa and therefore presumably recognize GPIIb/IIIa epitopes which are AITP-associated. Since the phage clones contain the antigen-binding sequences of natural autoantibodies which are derived from the genome of a healthy individual, this finding can lead to new insights into the origin of platelet-associated autoantibodies in AITP.

In addition to this, it is possible to use the novel phage clones to produce recombinant antiidiotypic antibodies against anti-GPIIb/IIIa autoantibodies, with the anti-GPIIb/IIIa phage clones being used as antigen. The recombinant antiidiotypic antibodies which can be obtained in this way constitute an attractive clinical alternative to using IVIgG.

The nucleotide sequences of the identified phage clones, and the amino acid sequences which are deduced from these nucleotide sequences, are depicted in the sequencing listings SEQ ID No. 1 to 8 (autoantibodies) and SEQ ID No. 9 to 18 (antiidiotypic antibodies).

I. Autoantibodies

A first aspect of the present invention relates to nucleic acids which encode auto-antibodies. Part of the subject-matter of the invention is therefore a nucleic acid which encodes the heavy chain of a human antibody, or a functional derivative or a fragment thereof, and encompasses a CDR3 region, selected from:

(a) a nucleotide sequence which encodes the amino acid sequence:
VLPFDPISMDV, (SEQ ID NO:31)
(b) a nucleotide sequence which encodes the amino acid sequence:
ALGSWGGWDHYMDV, (SEQ ID NO:32)
(c) a nucleotide sequence which encodes an amino acid sequence having an homology of at least 80%, and preferably at least 90%, with an amino acid sequence from (a) or (b), and
(d) a nucleotide sequence which encodes an amino acid sequence having an equivalent ability to bind to GPIIb/IIIa.

The novel nucleic acid furthermore preferably comprises a CDR1 region selected from:
- (a) a nucleotide sequence which encodes the amino acid sequence: GYSWR, (SEQ ID NO:33)
- (b) a nucleotide sequence which encodes the amino acid sequence: SYAMH, (SEQ ID NO:34) and
- (c) a nucleotide sequence which encodes an amino acid sequence having an homology of at least 80%, and preferably at least 90%, with an amino acid sequence from (a) or (b).

The novel nucleic acid preferably furthermore comprises a CDR2 region selected from:
- (a) a nucleotide sequence which encodes th amino acid sequence: DISYSGSTKYKPSLRS, (SEQ ID NO:35)
- (b) a nucleotide sequence which encodes the amino acid sequence: VISYDGSNKYYADSVKG, (SEQ ID NO:36) and
- (c) a nucleotide sequence which encodes an amino acid sequence having an homology of at least 80%, and preferably of at least 90%, with an amino acid sequence from (a) or (b).

A second aspect of the present invention is a nucleic acid which encodes the light chain of a human antibody, or a functional derivative or a fragment thereof, and comprises a CDR3 region, selected from:
- (a) a nucleotide sequence which encodes the amino acid sequence: ATWDDGLNGPV, (SEQ ID NO:37)
- (b) a nucleotide sequence which encodes the amino acid sequence: AAWDDSLNGWV, (SEQ ID NO:38)
- (c) a nucleotide sequence which encodes an amino acid sequence having an homology of at least 80%, and preferably of at least 90%, with an amino acid sequence from (a) or (b), and
- (d) a nucleotide sequence which encodes an amino acid sequence having an equivalent ability to bind to GPIIb/IIIa.

The novel nucleic acid preferably furthermore comprises a CDR1 region selected from:
- (a) a nucleotide sequence which encodes the amino acid sequence: SGSSSNIRSNPVS, (SEQ ID NO:39)
- (b) a nucleotide sequence which encodes the amino acid sequence: SGSSSNIGSNTVN, (SEQ ID NO:40) and
- (c) a nucleotide sequence which encodes an amino acid sequence having an homology of at least 80%, and preferably at least 90%, with an amino acid sequence from (a) or (b).

In addition, the novel nucleic acid preferably further comprises a CDR2 region selected from:
- (a) a nucleotide sequence which encodes the amino acid sequence: GSHQRPS, (SEQ ID NO:41)
- (b) a nucleotide sequence which encodes the amino acid sequence: SNNQRPS, (SEQ ID NO:42) and
- (c) a nucleotide sequence which encodes an amino acid sequence having an homology of at least 80%, and preferably at least 90%, with an amino acid sequence from (a) or (b).

II. Antiidiotypic antibodies

A second aspect of the present invention relates to nucleic acids which encode antiidiotypic antibodies. Part of the subject-matter of the invention is therefore a nucleic acid which encodes the heavy chain of a human antibody, or a functional derivative or a fragment thereof, and comprises a CDR3 region, selected from:
- (a) a nucleotide sequence which encodes the amino acid sequence: VRDLGYRVLSTFTFDI, (SEQ ID NO:43)
- (b) a nucleotide sequence which encodes the amino acid sequence: DGRSGSYARFDGMDV, (SEQ ID NO:44)
- (c) a nucleotide sequence which encodes the amino acid sequence: MGSSVVATYNAFDI, (SEQ ID NO:45)
- (d) a nucleotide sequence which encodes the amino acid sequence: DADGDGFSPYYFPY, (SEQ ID NO:46)
- (e) a nucleotide sequence which encodes the amino acid sequence: LRNDGWNDGFDI, (SEQ ID NO:47)
- (f) a nucleotide sequence which encodes the amino acid sequence: DSETAIAAAGRFDI, (SEQ ID NO:48)
- (g) a nucleotide sequence which encodes the amino acid sequence: EDGTTVPSQPLEF, (SEQ ID NO:49)
- (h) a nucleotide sequence which encodes the amino acid sequence: GSGSYLGYYFDY, (SEQ ID NO:50)
- (i) a nucleotide sequence which encodes the amino acid sequence: GLRSYNYGRNLDY, (SEQ ID NO:51)
- (j) a nucleotide sequence which encodes an amino acid sequence having an homology of at least 80%, and preferably at least 90%, with an amino acid sequence from (a), (b), (c) or (d), and
- (k) a nucleotide sequence which encodes an amino acid sequence having an equivalent ability to bind to autoantibodies against GPIIb/IIIa.

The novel nucleic acid furthermore preferably comprises a CDR1 region selected from: a nucleotide sequence which encodes the amino acid sequences NFAMS (SEQ ID NO:54), SYTMH (SEQ ID NO:55), DYALH (SEQ ID NO:56) OR SHYWS (SEQ ID NO:57) shown in Table 7a, a nucleotide sequence which encodes the amino acid sequence TYYWS (SEQ ID NO:58), a nucleotide sequence which encodes the amino acid sequences DYGMH (SEQ ID NO:59), SHTIS (SEQ ID NO:60), KYAIH (SEQ ID NO:61) or ELSMH (SEQ ID NO:62), shown in Table 7b and a nucleotide sequence which encodes an amino acid sequence having an homology of at least 80%, and preferably at least 90%, with one of the previously mentioned amino acid sequences.

Preferably, the novel nucleic acid furthermore comprises a CDR2 region selected from a nucleotide sequence which encodes the amino acid sequences GISGGGLLTHYA(D/N)SVKG (SEQ ID NO:63/SEQ ID NO:64), LISYDGSNKYYADSVKG (SEQ ID NO:111), GISWDSTSIGYADSVKG (SEQ ID NO:70) or FIYDGARTRFNPSLRS (SEQ ID NO:71) shown in Table 7a, a nucleotide sequence which encodes the amino acid sequence YIYYSGNTNYNPSLKS (SEQ ID NO:112), a nucleotide sequence which encodes the amino acid sequences AISYDGSNKYYADSVFG (SEQ ID NO:113), GITPIFGTVNYAQKFQG (SEQ ID NO:65), AISSNGGNTYYADSVKG (SEQ ID NO:72) or GFD-PEDGETIYAQKFQG (SEQ ID NO:73) shown in Table 7b, and a nucleotide sequence which encodes an amino acid sequence having an homology of at least 80%, and preferably of at least 90%, with one of the previously mentioned amino acid sequences.

Another part of the subject-matter of the present invention is a nucleic acid which encodes the light chain of a human antibody, or a functional derivative or a fragment thereof, and comprises a CDR3 region, selected from:
(a) a nucleotide sequence which encodes the amino acid sequence:
CSYVHSSTN, (SEQ ID NO:52)
(b) a nucleotide sequence which encodes the amino acid sequence:
QVWDNTNDQ, (SEQ ID NO:53)
(c) a nucleotide sequence which encodes an amino acid sequence having an homology of at least 80%, and preferably at least 90%, with an amino acid sequence from (a), and
(d) a nucleotide sequence which encodes an amino acid sequence having an equivalent ability to bind to autoantibodies against GPIIb/IIIa.

Preferably, the novel nucleic acid furthermore comprises a CDR1 region selected from a nucleotide sequence which encodes the amino acid sequence TGTS SAIGNYNFVP (SEQ ID NO:66) shown in a 7a, a nucleotide sequence which encodes the amino acid sequence GGYK IGSKSVH shown in Tab. 7b (SEQ ID NO:67) and a nucleotide sequence which encodes an amino acid sequence having an homology of at least 80%, and preferably of at least 90%, with the previously mentioned amino acid sequence.

In addition, the novel nucleic acid preferably furthermore comprises a CDR2 region selected from a nucleotide sequence Which encoders the amino acid sequence EGSKRPS (SEQ ID NO:68) shown in Tab. 7a, a nucleotide sequence which encodes the amino acid sequence EDSY RPS (SEQ ID NO:69) shown in Tab. 7b, and a nucleotide sequence which encodes an amino acid sequence having an homology of at least 80%, and preferably at least 90%, with the previously mentioned amino acid sequence.

Within the meaning of the present invention, the phrase "functional derivative of a chain of a human antibody" is to be understood as meaning a polypeptide which encompasses at least a CDR3 region or the heavy and/or light chain, as defined above, and which is able, where appropriate together with the relevant complementary chain of the human antibody (or a derivative of such a chain), to form an antibody derivative which possesses a recognition specificity for an antigen which is equivalent to that possessed by the non-derivatized antibody. Preferably, such an antibody derivative has a binding constant for the relevant antigen of at least $10^{-6}$ 1/mol, preferably of at least $10^{-3}$ 1/mol.

Functional derivatives of chains of a human antibody can be prepared, for example, by using recombinant DNA techniques to delete, substitute and/or insert segments of the gene encoding the relevant polypeptide.

Single-chain antibodies, which can, for example, be composed of the variable domains of he H and L chains or one or two H chain domains and, where appropriate a constant domain, are particularly preferred functional derivatives of antibody chains or antibodies. The preparation of such constructs is described in Hoogenboom et al., Immunol. Rev. 130 (1992), 41–68; Barbas III, Methods: Companion Methods Enzymol. 2 (1991), 119 and Plückthun, Immunochemistry (1994), Marcel Dekker Inc., Chapter 9, 210–235.

Within the meaning of the present invention, the phrase "equivalent ability to bind" is to be understood as being a binding affinity and/or specificity, i.e. epitope recognition, which is the same as that in the specifically disclosed sequences.

Another part of the subject-matter of the present invention is a vector which contains at least one copy of a novel nucleic acid. This vector can be a prokaryotic vector or a eukaryotic vector. Plasmids, cosmids and bacteriophages are examples of prokaryotic vectors. Such vectors are, for example, described in detail in Chapters 1 to 4 in Sambrook et al., Molecular Cloning. A Laboratory Manual, 2nd edition (1989), Cold Spring Harbor Laboratory Press. A prokaryotic vector is preferably a plasmid or a phage.

On the other hand, the vector can also be a eukaryotic vector, e.g. a yeast vector, an insect vector (baculovirus) or a mammalian vector (plasmid vector or viral vector). Examples of eukaryotic vectors are described in Sambrook at al., loc. cit., Chapter 16, and Winnacker, Gene und Klone, Eine Einführung für die Gentechnologie [Genes and clones, an introduction to genetic engineering] (1985), VCH Verlagsgesellschaft, in particular Chapters 5, 8 and 10.

Yet another part of the subject-matter of the present invention is a cell which expresses a novel nucleic acid, or a cell which is transformed with a novel nucleic acid or with a novel vector. The cell can be a prokaryotic cell (e.g. a Gram-negative bacterial cell, in particular E.coli) or a eukaryotic cell (e.g. a yeast, plant or mammalian cell). Examples of suitable cells and methods for introducing the novel nucleic acid into such cells can be found in the above literature references.

Another part of the subject-matter of the present invention is a polypeptide which is encoded by a novel nucleic acid, in particular a recombinant polypeptide. Particularly preferably, the polypeptide contains the variable domain of the H chain and/or L chain of a human antibody.

Particular preference is given to a polypeptide which exhibits antibody properties and whose subunit components are a heavy chain, or a functional derivative thereof, and a light chain, or a functional derivative thereof. The polypeptide can be composed of two separate chains or be present as a single-chain polypeptide.

Yet another part of the subject-matter of the present invention is an antibody against a novel polypeptide, which antibody is directed against a region of the polypeptide which is responsible for recognizing the antigen. This antibody can be a polyclonal antiserum, a monoclonal antibody or a fragment of a polyclonal or monoclonal antibody (e.g. a Fab, F(ab)$_2$, Fab' or F(ab')$_2$ fragment). The antibody is preferably directed against the CDR3 region of the heavy and/or light antibody chain of the novel polypeptide, or a region thereof. Known methods can be used to obtain such antibodies by immunizing an experimental animal with a peptide or polypeptide which contains a novel CDR3 region and isolating the resulting polyclonal antibody from the experimental animal. In addition, monoclonal antibodies can be obtained by fusing an antibody-producing B cell from the experimental animal with a leukaemia cell in accordance with the method of Kohler and Milstein or a further development of this method. In addition, recombinant antibodies which are directed against the CDR3 region of the novel polypeptide can also be obtained by screening a suitable phagemid library, e.g. a phagemid library from a healthy human donor, with a novel polypeptide being used as the antigen.

The invention also relates to a pharmaceutical composition which comprises a nucleic acid, a vector, a polypeptide, an antibody or a cell as previously mentioned, as active component, where appropriate together with other active components and also pharmaceutically customary adjuvants, additives or excipients.

The pharmaceutical composition can be used for preparing a diagnostic or therapeutic agent. Examples of diagnostic uses are the diagnosis of AITP or of a predisposition for AITP. Another preferred diagnostic use is that of monitoring the course of the AITP disease.

The use of the pharmaceutical composition as a diagnostic agent can comprise, for example, detecting a B cell subpopulation which is expressing a novel polypeptide as the antibody. This antibody can be detected, for example, at the nucleic acid level, e.g. by means of a nucleic-acid-hybridization assay, together with prior amplification where appropriate. On the other hand, the antibody can also be detected as to the protein level by means of an immunoassay using antigens or antibodies which react specifically wish the polypeptide.

Furthermore, the novel pharmaceutical composition can also be applied in the therapeutic field, in particular for the prevention or therapy of AITP. This therapeutic use can, for example, be based on stimulating the production of anti-autoantibodies. For this, the novel autoantibody polypeptide can, for example, be administered to a patient, thereby eliciting and/or stimulating the formation of antiidiotypic antibodies. In this connection, this administration can be effected in accordance with customary immunization protocols (Fox et al., J. Pharmacol. Exp. Ther. 279 (1996), 1000–1008; Whittum-Hudson et al., Nat. Med. 2 (1996), 1116–1121; Jardieu, Curr. Opin. Imunol. 7 (1995), 779–782). On the other hand, the expression of antibody genes can be inhibited specifically by administering suitable antisense nucleic acids. The novel antiidiotypic antibody polypeptide can be administered to a patient in order to achieve direct inhibition of the autoantibody activity.

Investigations carried out on the novel autoantibody polypeptides have shown that these polypeptides are surprisingly able to inhibit the binding of fibrinogen to blood platelets. The novel autoantibody polypeptides and antiidiotypic antibody polypeptides can therefore be employed, where appropriate in combination, as agents for modulating blood coagulation, in particular for preventing a thrombosis, for example following cardiac infarctions or strokes, or in association with venous thromboses together with lung embolisms or ischaemias, etc.

Murine monoclonal antibodies, e.g. the monoclonal antibody 7E3 (cf., e.g., U.S. Pat. No. 5,440,020) or fragments thereof (e.g. the commercially available Fab fragment ReoPro®), or short synthetic peptides, have hitherto been used as fibrinogen antagonists for therapeutic purposes. However, murine monoclonal antibodies and antibody fragments suffer from the disadvantage that, as a result of their immunogenicity, they give rise to undesirable side reactions when used for treating human patients, while short peptides are generally degraded very rapidly. As compared with these known agents, the novel polypeptides have the advantage that they consist of amino acid sequences of human origin and therefore exhibit fewer undesirable side effects than do corresponding murine antibodies or antibody fragments, and that, because of their size, they are not subjected to such rapid degradation as are peptides.

The invention therefore relates to the use of a novel nucleic acid, in particular a nucleic acid which encodes an autoantibody polypeptide, of a vector which contains this nucleic acid, of a cell which is transformed with the nucleic acid or the vector, of a polypeptide which is encoded by the nucleic acid, or of a pharmaceutical composition which comprises one or more of the said substances, for preparing an agent for affecting and in particular inhibiting the binding of fibrinogen to blood platelets. Preference is given to using the agent for modulating blood coagulation, in particular for dissolving thrombi and/or for preventing the formation of thrombi. The administration of the novel pharmaceutical composition can be effected in accordance with protocols which have already been established for murine antibodies or antibody fragments.

Yet another part of the subject-matter of the invention is a process for isolating phagemid clones which express nucleic acids which encode autoantibodies against GPIIb/IIIa or encode antiidiotypic antibodies which are directed against these autoantibodies, characterized in that a phagemid library is prepared from lymphocytes from a human donor and the desired phagemid clones are isolated by affinity selection, comprising negative and positive selection steps. Preferably, the process also involves isolating antibody-encoding nucleic acids from the clones and/or using the antibody-encoding nucleic acids for expressing recombinant antibody chains or derivatives or fragments thereof.

The invention is also explained by the following examples, figures and sequence listings, in which SEQ ID No. 1 shows the nucleotide sequence of the H chain of a novel antibody (phagemid clone PDG7), with framework region (FR)1 extending from bp 1 to 90, complement-determining region (CDR)1 from bp 91 to 105, FR2 from bp 106 to 147, CDR2 from bp 148 to 195, FR3 from bp 196 to 291, CDR3 from bp 292 to 324 and FR4 from bp 325 to 357, SEQ ID No.2 shows the amino acid sequence corresponding to the nucleotide sequence depicted in SEQ ID No.1, with FR1 extending from AA 1 to 30, CDR1 from AA 31 to 35, FR2 from AA 36 to 49, CDR2 from AA 50 to 65, FR3 from AA 66 to 97, CDR3 from AA 98 to 108 and FR4 from AA 109 to 119, SEQ ID No.3 shows the nucleotide sequence of the L chain of a novel polypeptide (phagemid clone PDG7), with FR1 extending from bp 1 to 60, CDR1 from bp 61 to 99, FR2 from bp 100 to 144, CDR2 from bp 145 to 165, FR3 from bp 166 to 261, CDR3 from bp 262 to 294 and FR4 from bp 295 to 333, SEQ ID No.4 shows the amino acid sequence corresponding to the nucleotide sequence given in SEQ ID No. 3, with FR1 extending from AA 1 to 20, CDR1 from AA 21 to 33, FR2 from AA 34 to 48, CDR2 from AA 49 to 55, FR3 from AA 56 to 87, CDR3 from AA 88 to 98 and FR4 from AA 99 to 11 [sic], SEQ ID No.5 shows the nucleotide sequence of the H chain of a novel polypeptide (phagemid clone PDG13), with FR1 extending from bp 1 to 90, CDR1 from bp 91 to 109, FR2 from bp 106 to 147, CDR2 from bp 148 to 198, FR3 from bp 199 to 294, CDR3 from bp 295 to 336 and FR4 from bp 337 to 369, SEQ ID No.6 shows the amino sequence corresponding to the nucleotide sequence depicted in SEQ ID No.5, with FR1 extending from AA 1 to 30, CDR1 from AA 31 to 35, FR2 from AA 36 to 49, CD2 from AA 50 to 66, FR3 from AA 67 to 98, CDR3 from AA 99 to 112 and FR4 from AA 113 to 123, SEQ ID No.7 shows the nucleotide sequence of the L chain of a novel polypeptide (phagemid clone PGD13), with FR1 extending from bp 1 to 60, CDR1 from bp 61 to 99, FR2 from bp 100 to 144, CDR2 from bp 145 to 165, FR3 from bp 166 to 261, CDR3 from bp 262 to 294 and FR4 from bp 295 to 333, SEQ ID No.8 shows the amino acid sequence of the nucleotide sequence depicted in SEQ ID No. 7, with FR1 extending from AA 1 to 20, CDR1 from AA 21 to 33, FR2 from AA 34 to 48, CDR2 from AA 49 to 55, FR3 from AA 56 to 87, CDR3 from AA 88 to 98 and FR4 from AA 99 to 111, SEQ ID No.9 shows the nucleotide sequence of the H chain of a novel polypeptide (phagemid clone AI-X16), with FR1 extending from bp 1 to 90, CDR1 from bp 91 to 105, FR2 from bp 106 to 147, CDR2 from bp 148 to 198, FR3 from bp 199 to 288, CDR3 from bp 289 to 336 and FR4 from bp 337 to 369, SEQ ID No.10 shows the amino acid sequence of the nucleotide sequence depicted in SEQ ID No. 9, with FR1 extending from AA 1 to 30, CDR1 from AA 31 to 35, FR2 from AA 36 to 49, CDR2 from AA 50 to 66, FR3 from AA 67 to 96, CDR3 from AA 97 to 112 and FR4 from AA 113 to 123, SEQ ID No. 11 shows the nucleotide sequence of the L chain of a novel polypeptide (phagemid clone AI-X16), with FR1 extending from bp 1 to 60, CDR1 from bp 61 to 102, FR2 from bp 103 to 147, CDR2 from bp 148 to 168, FR3 from bp 169 to 264, CDR3 from [lacuna] 265 to 291 and FR4 from bp 292 to 375, SEQ ID No. 12 shows the amino acid sequence of the nucleotide sequence depicted in SEQ ID No. 11, with FR1 extending from AA 1 to 20, CDR1 from AA 21 to 34, FR2 from AA 35 to 49, CDR2 from AA 50 to 56, FR3 from AA 57 to 88, CDR3 from AA 89 to 97 and FR4 from AA 89 to 125, SEQ ID No. 13 shows the nucleotide sequence of the H chain of a novel polypeptide (phagemid clone AI-X20), with FR1 extending from bp 1 to 90, CDR1 from bp 91 to 105, FR2 from bp 106 to 147, CDR2 from bp 148 to 195, FR3 from bp 196 to 291, CDR3 from bp 292 to 333 and FR4 from bp 334 to 366, SEQ ID No. 14 shows the amino acid sequence of the nucleotide sequence depicted in SEQ ID No. 13, with FR1 extending from AA 1 to 30, CDR1 from AA 31 to 35, FR2 from AA 36 to 49, CDR2 from AA 50 to 65, FR3 from AA 66 to 97, CDR3 from AA 98 to 111 and FR4 from AA 112 to 122, SEQ ID No. 15 shows the nucleotide sequence of the H chain of a novel polypeptide (phagemid clone AI-X39), with FR extending from bp 1 to 90, CDR1 from bp 91 to 105, FR2 from bp 106 to 147, CDR2 from pb [sic] 148 to 198, FR3 from bp 199 to 294, CDR3 from bp 295 to 339 and FR4 from 340 to 372, SEQ ID No. 16 shows the amino acid sequence of the nucleotide sequence depicted in SEQ ID No. 15, with FR1 extending from AA 1 to 30, CDR1 from AA 31 to 35, FR2 from AA 36 to 49, CDR2 from AA 50 to 66, FR3 from AA 67 to 98, CDR3 from AA 99 to 113 and FR 4 from AA 114 to 124, SEQ ID No. 17 shows the nucleotide sequence of the H chain of a novel polypeptide (phagemid clone AI-X40), with FR1 extending from bp 1 to 90, CDR1 from bp 91 to 105, FR2 from bp 106 to 147, CDR2 from bp 148 to 198, FR3 from bp 199 to 297, CDR3 from bp 298 to 339 and FR4 from bp 340 to 372, SEQ ID No. 18 shows the amino acid sequence of the nucleotide sequence depicted in SEQ ID No. 17, with FR1 extending from AA 1 to 30, CDR1 from AA 31 to 35, FR2 from AA 36 to 49, CDR2 from AA 50 to 66, FR3 from AA 67 to 99, CDR3 from AA 100 to 113 and FR4 from AA 114 to 124, SEQ ID No. 19 shows the nucleotide sequence of the H chain of a novel polypeptide (phagemid clone AI-X2), with FR1 extending from bp 1 to 90, CDR1 from bp 91 to 105, FR2 from bp 106 to 147, CDR2 from bp 148 to 195, FR3 from bp 196 to 291, CDR3 from bp 292 to 327 and FR4 from bp 328 to 360, SEQ ID No. 20 shows the amino acid sequence of the nucleotide sequence depicted in SEQ ID No. 19, with FR1 extending from AA 1 to 30, CDR1 from AA 31 to 35, FR2 from AA 36 to 49, CDR2 from AA 50 to 65, FR3 from AA 66 to 97, CDR3 from AA 98 to 109 and FR4 from AA 110 to 120, SEQ ID No. 21 shows the nucleotide sequence of the H chain of a novel polypeptide (phagemid clone AI-B14), with FR1 extending from bp 1 to 90, CDR1 from bp 91 to 105, FR2 from bp 106 to 147, CDR2 from bp 148 to 198, FR3 from bp 199 to 294, CDR3 from bp 295 to 336 and FR4 from bp 337 to 369;

The following variations in the sequence were also found: a C can be present at position 7, while a G can be present at position 9, a G at position 13, a G at position 15, an A at position 91, a G at position 92, a C at position 98, a T at position 149, an A at position 205, an A at position 228, an A at position 251, a T at position 253 and/or an A at position 284. The consequence of this is that, in the amino acid sequence (cf. SEQ ID No. 22), a Q can be present at position 3, while a V can be present at position 5, an S at position 31, an A at position 33, a V at position 50, a T at position 69, a K at position 76, an N at position 84, an S at position 85 and/or a Y at position 95.

SEQ ID No. 22 shows the amino acid sequence of the nucleotide sequence depicted in SEQ ID No. 21, with FR1 extending from AA 1 to 30, CDR1 from AA 31 to 35, FR2 from AA 36 to 49, CDR2 from AA 50 to 66, FR3 from AA 67 to 98, CDR3 from AA 99 to 112 and FR4 from AA 113 to 123, SEQ ID No. 23 shows the nucleotide sequence of the H chain of a novel polypeptide (phagemid clone AI-B18), with FR1 extending from bp 1 to 90, CDR1 from bp 91 to 105, FR2 from bp 106 to 147, CDR2 from bp 148 to 198, FR3 from bp 199 to 294, CDR3 from bp 295 to 333 and FR4 from bp 334 to 366;

The following variations in the nucleotide sequence were also found: thus, a C can be present at position 7, while a G can be present at position 13, a C at position 16, an A at position 56, a T at position 94, a G at position 97, a T at position 155, a C at position 173, a T at position 223, a T or a C at position 252, a G at position 261, a G at position 267, an A at position 271, a C at position 275 and/or a G at position 277. The consequence of this is that, in the corresponding amino acid sequence (cf. SEQ ID No. 24), a Q can be present at position 3, while a V can be present at position 5, a Q at position 6, a K at position 19, a Y at position 32, an A at position 33, an I at position 52, an A at position 58, an S at position 75, an S at position 84, an R at position 87, an E at position 89, a T at position 91, an A at position 92 and/or a V at position 93.

SEQ ID No. 24 shows the amino acid sequence of the nucleotide sequence depicted in SEQ ID No. 23, with FR1 extending from AA 1 to 30, CDR1 from AA 31 to 35, FR2 from AA 36 to 49, CDR2 from AA 50 to 66, FR3 from AA 67 to 98, CDR2 from AA 99 to 111 and FR4 from AA 112 to 122, SEQ ID No. 25 shows the nucleotide sequence of the H chain of a novel polypeptide (phagemid clone AI-B24), with FR1 extending from bp 1 to 90, CDR1 from bp 91 to 105, FR2 from bp 106 to 147, CDR2 from bp 148 to 198, FR3 from bp 199 to 294, CDR3 from bp 295 to 330 and FR4 from bp 331 to 363;

The following variations in the nucleotide sequence were also found: a C can be present at position 7, while a G can be present at position 9, a G at position 13, a G at position 15, a G at position 31, an A at position 46, a G at position 67, a G at position 89, a G at position 92, a C at position 93, a G at position 98, a G at position 102, a G at position 140, a C at position 141, a G at position 145, a T at position 149, a T at position 157, an A at position 158, a G at position 160, an A at position 166, an A at position 173, a T at position 235, an A at position 251, a C at position 290 and/or an A at position 293. The consequence of this is that, in the corresponding amino acid sequence (cf. SEQ ID No. 26), a Q can be present at position 3, while a V can be present at position 5, a V at position 11, an R at position 16, an A at position 23, an S at position 30, an S at position 31, a G at position 33, an M at position 34, a W at position 47, an A at position 49, a V at position 50, a Y at position 53, a D at position 54, an S at position 56, a K at position 58, an L at position 79, an N at position 84, an A at position 97 and/or a K at position 98.

SEQ ID No. 26 shows the amino acid sequence of the nucleotide sequence depicted in SEQ ID No. 25, with FR1 extending from AA 1 to 30, CDR1 from AA 31 to 35, FR2 from AA 36 to 49, CDR2 from AA 50 to 66, FR3 from AA 67 to 98, CDR3 from AA 99 to 110 and FR4 from AA 111 to 121, SEQ ID No. 27 shows the nucleotide sequence of the L chain of a novel polypeptide (phagemid clone AI-B24), with FR1 extending from bp 1 to 60, CDR1 from bp 61 to 96, FR2 from bp 97 to 138, CDR2 from bp 139 to 159, FR3 from bp 160 to 255, CDR3 from bp 256 to 282 and FR4 from bp 283 to 366;

The following variations in the nucleotide sequence were also found: a C or a T can be present at position 4, while a G can be present at position 37, an A at position 40, a G at position 50, an A at position 67, a T at position 72, an A at position 133, a T at position 136, a T or a C at position 138, a G at position 148, a T at position 160, a T at position 161, a T or a C at position 162, a C at position 200, a T at position 217, a G at position 218, an A or a C at position 220, a G at position 269, a T at position 271, a G at position 272, a G at position 275 and/or a T or a C at position 282. The consequence of this is that, in a corresponding amino acid sequence (cf. SEQ ID No. 28), an L can be present at position 2, while a G can be present at position 13, a K at position 14, an R at position 17, an N at position 23, an N at position 24, an I at position 45, a Y at position 47, a D at position 50, an F at position 54, a T at position 67, an S at position 73, an R at position 74, an S at position 90, an S at position 91, an S at position 92 and/or an H at position 94.

SEQ ID No. 28 shows the amino acid sequence of the nucleotide sequence depicted in SEQ ID No. 27, with FR1 extending from AA 1 to 20, CDR1 from AA 21 to 32, FR2 from AA 33 to 46, CDR2 from AA 47 to 53, FR3 from AA 54 to 85, CDR3 from AA 86 to 94 and FR4 from An 95 to 122, SEQ ID No. 29 shows the nucleotide sequence of the H chain of a novel polypeptide (phagemid clone AI-B38), with FR1 extending from bp 1 to 90, CDR1 from bp 91 to 105, FR2 from bp 106 to 147, CDR2 from bp 148 to 198, FR3 from bp 199 to 294, CDR3 from bp 295 to 333 and FR4 from bp 334 to 366;

The following variations in the nucleotide sequence were also found: a C can be present at position 7, while a G can be present at position 9, a G at position 13, an A at position 15 and/or a C at position 16. The consequence of this is that, in the corresponding amino acid sequence, a Q can be present at position 3, while a V can be present at position 5 and/or a Q can be present at position 6, and SEQ ID No. 30 shows the amino acid sequence of the nucleotide sequence depicted in SEQ ID No. 29, with FR1 extending from AA 1 to 30, CDR1 from AA 31 to 35, FR2 from AA 36 to 49, CDR2 from AA 50 to 66, FR3 from AA 67 to 98, CDR3 from AA 99 to 111 and FR4 from AA 112 to 122.

FIG. 1 shows the inhibition of the binding of autoantibody phabs (PDG-X) to GPIIb/IIIa which is brought about by adding the antiidiotypic antibody phab AI-X17.

Figure 2:
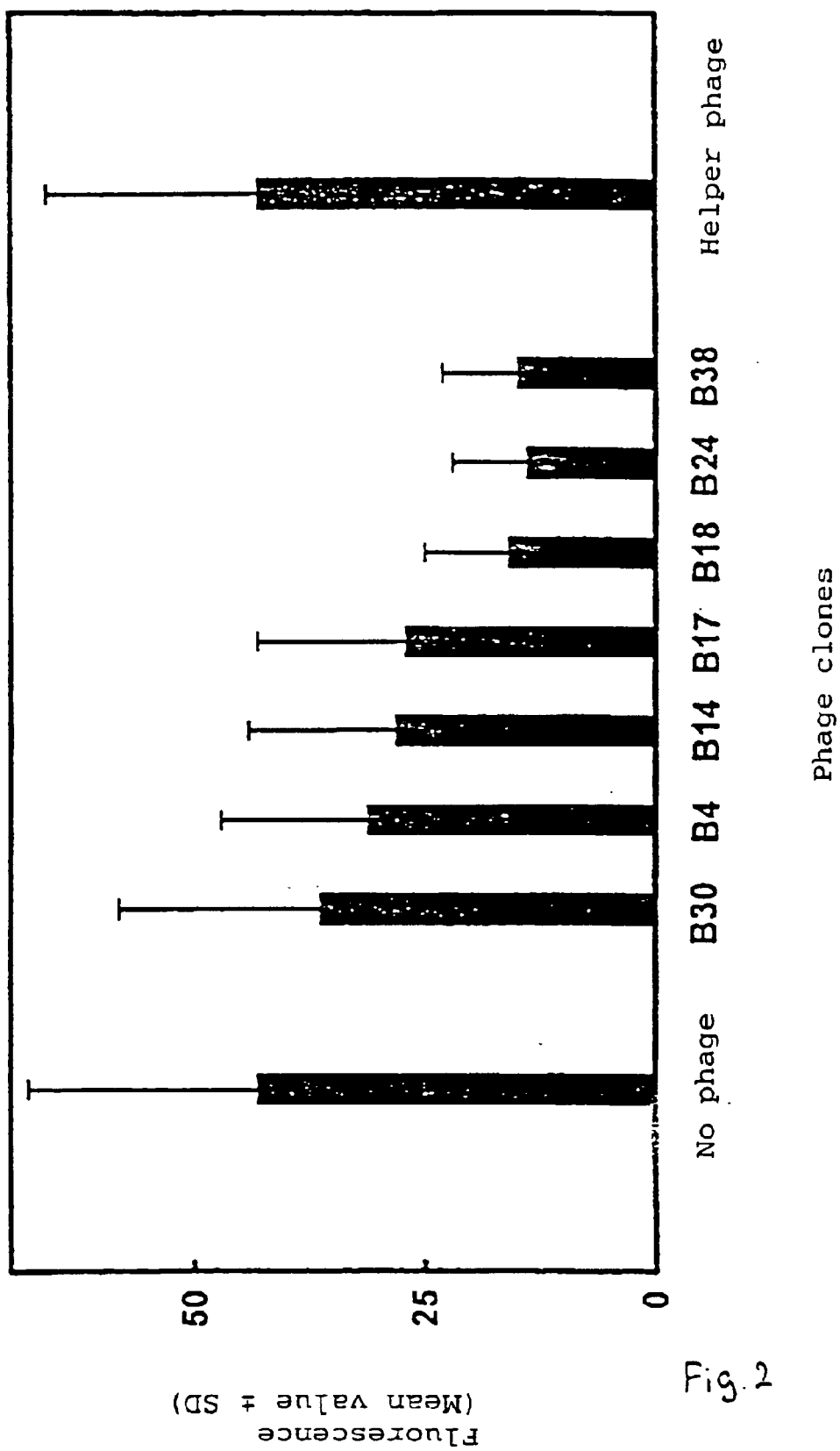
Figure 3:
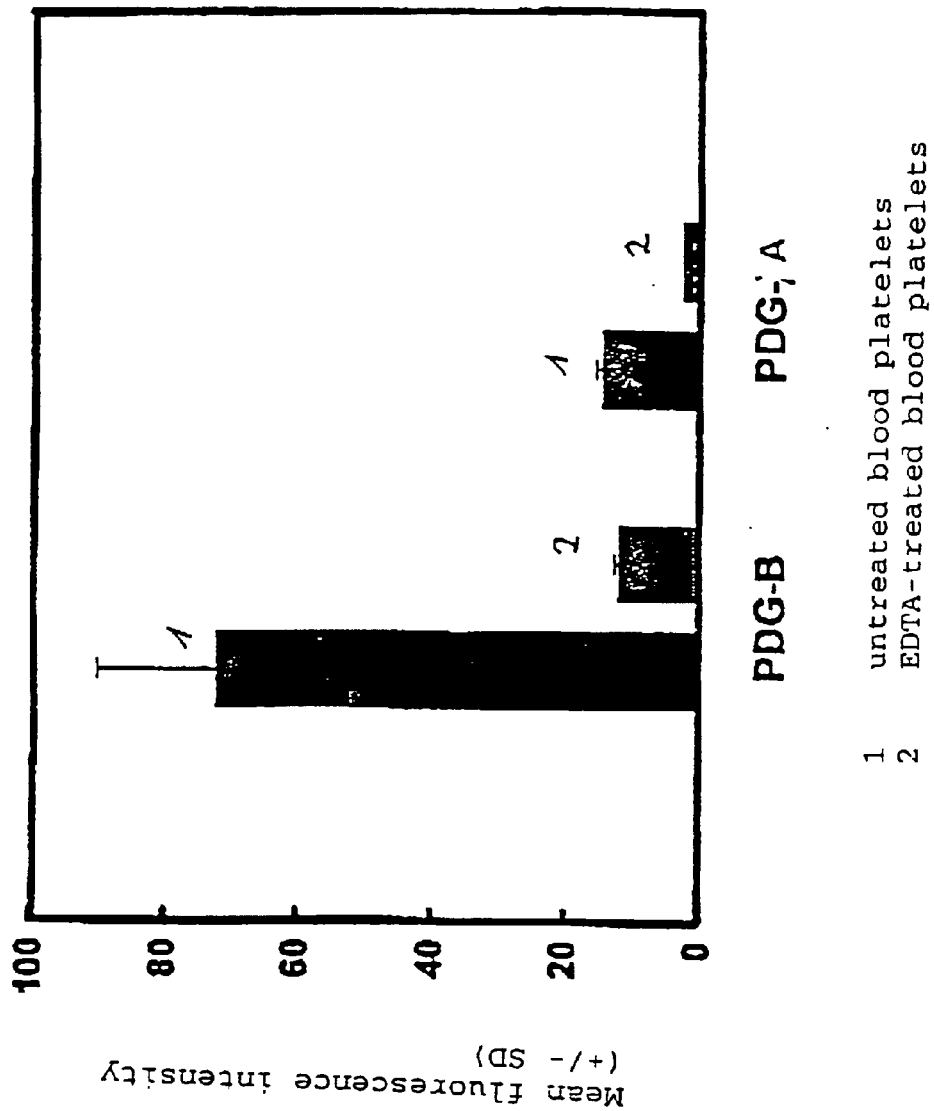
Figure 4:
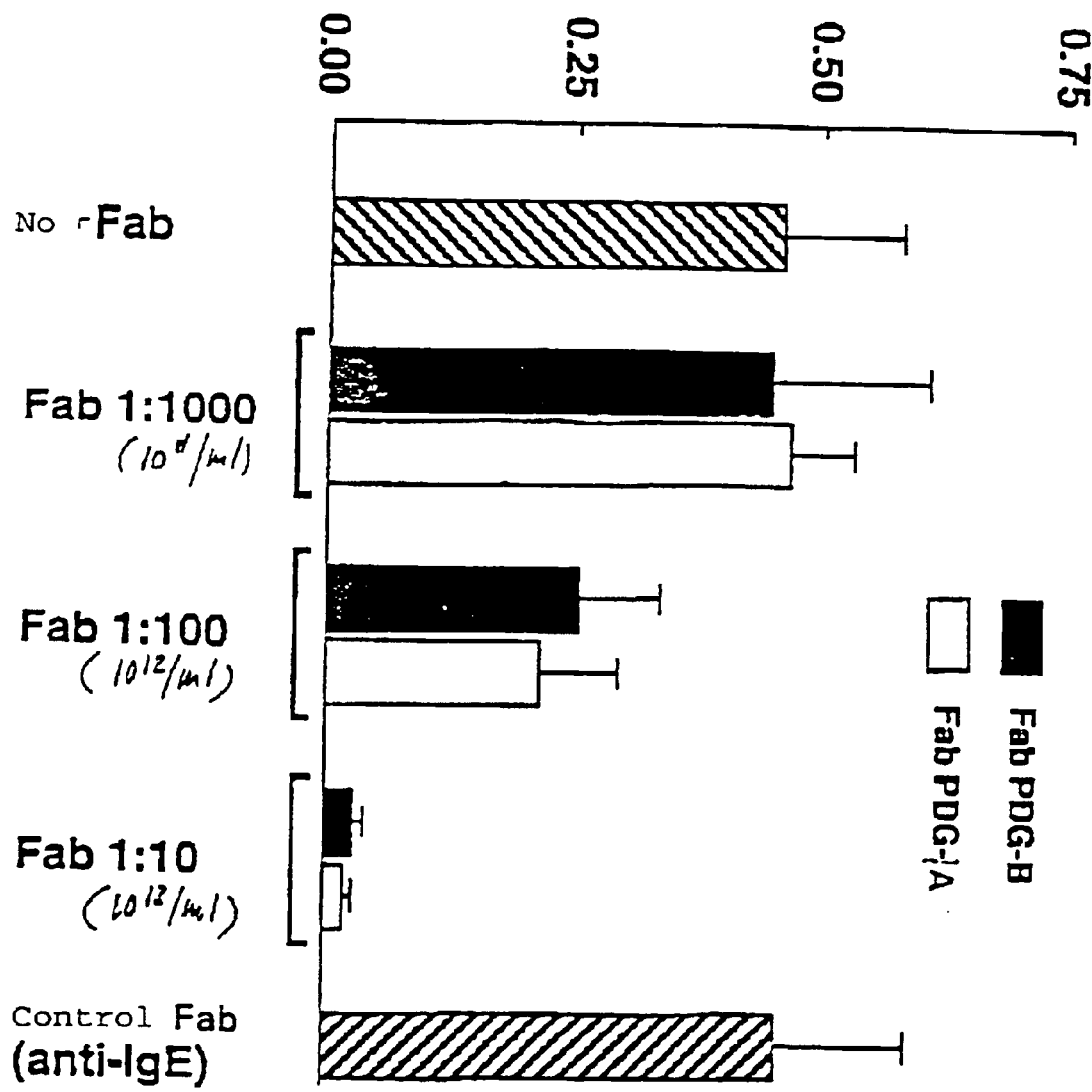
Figure 5:
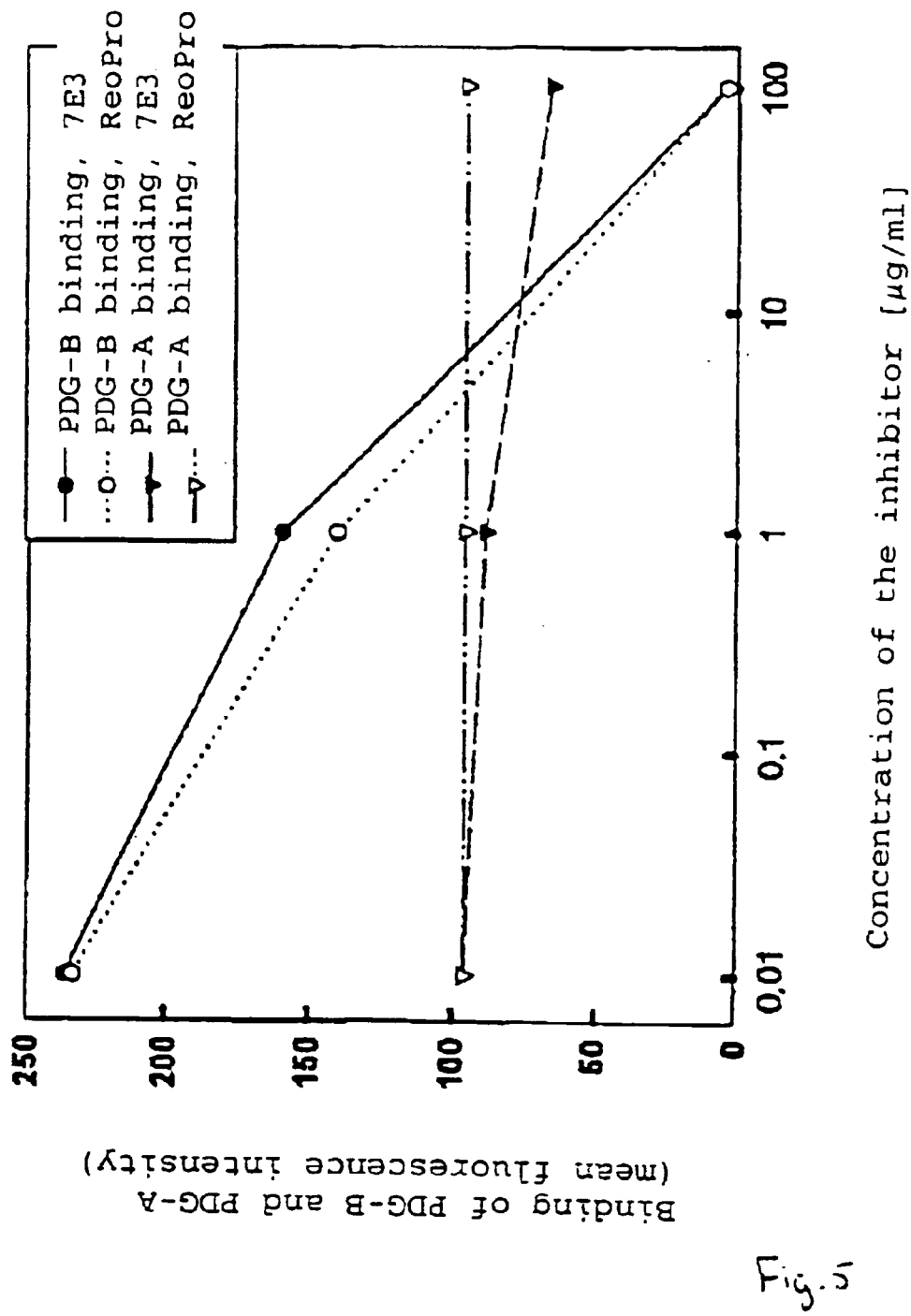
Figure 6:
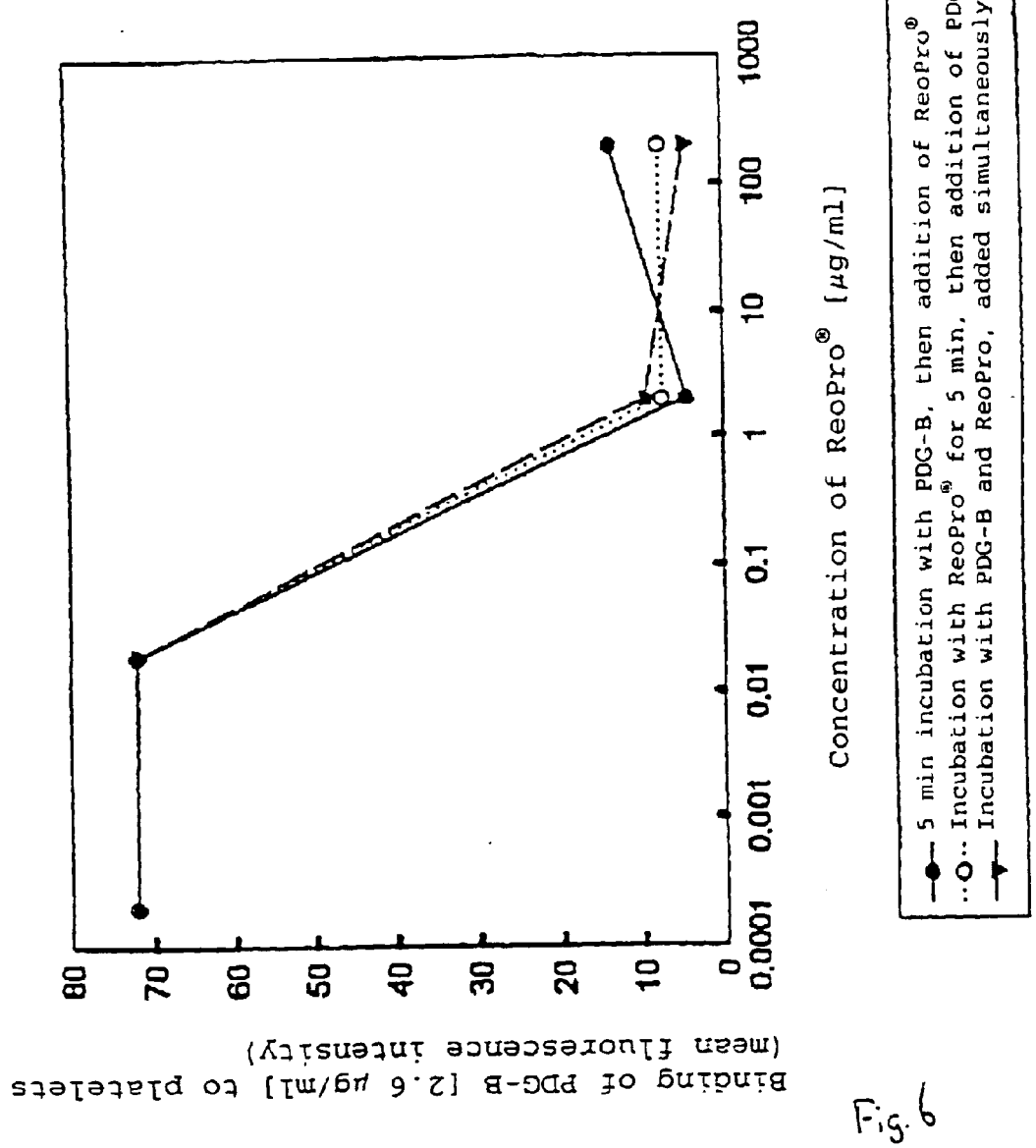
Figure 7:
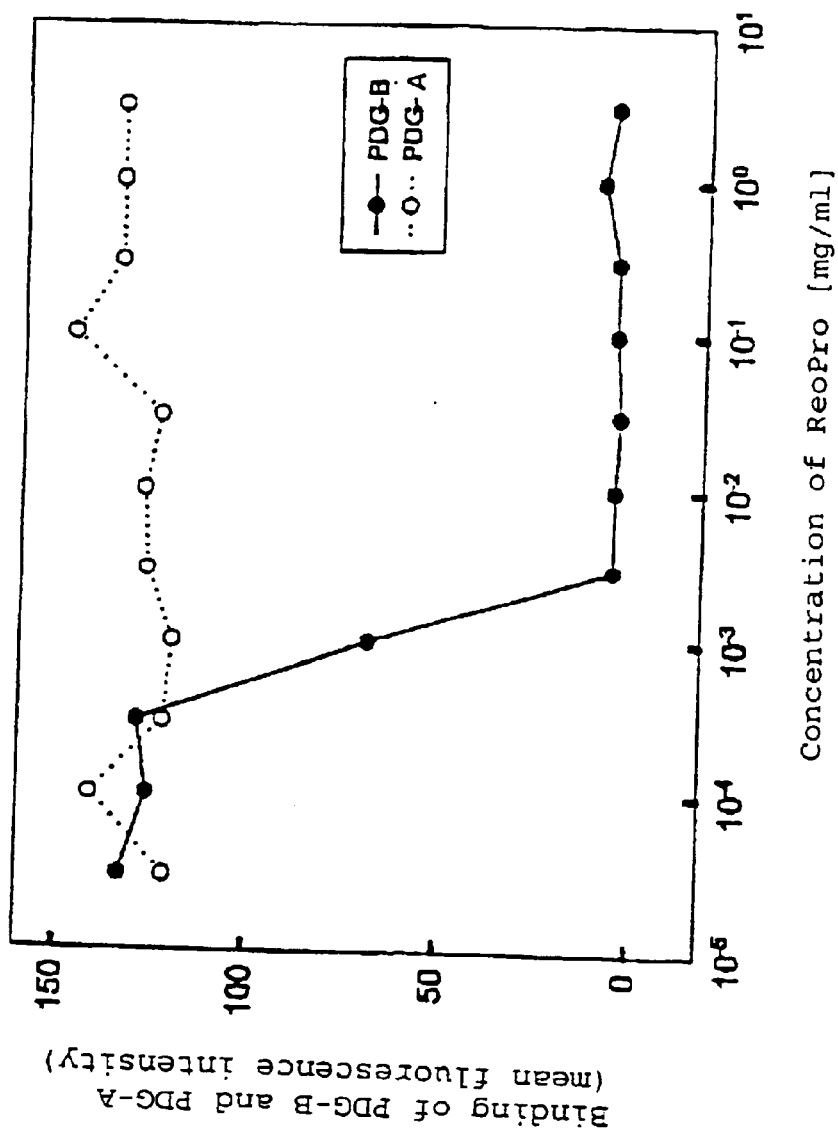

FIG. 2 shows the inhibition of the binding of autoantibody phabs (PDG-B) to blood platelets which is brought about by antiidiotypic antibody phabs AI-B, FIG. 3 shows the binding of autoantibody phabs to untreated and EDTA-treated blood platelets, FIG. 4 shows the inhibition of the binding of fibrinogen to GPIIb/IIIa which is brought about by autoantibody phabs, FIGS. 5–7 show the inhibition of the binding of autoantibody phabs to GPIIb/IIIa which is brought about by the antibody 7E3 and the antibody fragment ReoPro®.

EXAMPLES

1. Identification of Autoantibody Sequences 1.1. Isolation of Autoantibodies

Autoantibodies were obtained from 12 AITP patients (8 suffering from primary AITP, 3 suffering from AITP associated with SLE, 1 suffering from AITP associated with Sjögren's syndrome) by incubating patient plasma with purified GPIIb/IIIa at 4° C. overnight and subsequently eluting, at room temperature for 15 min, in 0.2 mol/l glycine and 0.15 mol/l NaCl, pH 2.5. After centrifuging at 100,000 g for 30 min, the supernatant was neutralized with 1 mol/l Tris-HCl and dialysed overnight against Tris-buffered salt solution (TBS).

At the time of plasma withdrawal, all the patients were thrombocytopenic (platelet count<150×10$^9$/l) and had normal or enlarged megakaryocytes in the bone arrow and were free of other detectable forms of immunothrombocytopenia.

1.2. Isolation of Purified Antigens

The antigens used were purified GPIIb/IIIa, a cytoplasmic fragment of GPIIIa (amino acids 721–744) and an extracellular fragment of GPIIIa (amino acids 468–690) (Beardsley, Blut 59 (1989), 47–51 and Phillips et al., Methods Enzymol. 215 (1992), 244–263).

1.3. Isolation of Platelets for Panning and Immunoblotting

Platelet-enriched plasma was prepared by differential centrifugation from EDTA-anticoagulated blood samples taken from healthy human donors. The platelets were isolated by centrifuging at 2000 g for 15 min, then washed six times in citric acid buffer (pH 6.2) containing 50 mmol/l sodium citrate, 100 mmol/l NaCl and 125 mmol/l glucose, and finally resuspended in the same buffer.

The same enrichment protocol was used to obtain thrombasthenic platelets from a 14-year-old boy suffering from Glanzmann's type I thrombasthenia.

1.4. Monoclonal Antibodies

Use was made of murine monoclonal antibodies which recognize the complexed form of GPIIb/IIIa and of antibodies which recognize GPIIb or GPIIIa selectively. These antibodies were isolated by means of customary immunization protocols using the corresponding antigens and are not AITP-associated. The isolation of such antibodies is described in Kouns et al. (J. Biol. Chem. 267 (1992), 18844–18851), Steiner et al. (Biochim. Biophys. Acta 1119

(1992), 12–21) and Häring et al. (Proc. Natl. Acad. Sci. USA 82 (1985), 4837–4841).

1.5. Phagemid Library

A combinatorial Fab library was prepared in accordance with the method described by Vogel et al. (Eur. J. Immunol. 24 (1994), 1200–1207) using peripheral blood lymphocytes obtained from a healthy, preimmunized human donor. All the enzymes and oligonucleotides were obtained from Boehringer Mannheim GmbH (Mannheim, Germany) apart from the Taq polymerase (Perkin Elmer, N.J., USA). The primers for amplifying the H and L chains of the Fab molecules by PCR, the VCSM13 helper phage, and the *Escherichia coli* strain XL-Blue were obtained from Stratacyte (La Jolla, Calif., USA) The phagemid pComb3 was obtained from Scripps Research Institute (La Jolla, Calif., USA). The cloning, the transformation into XL-Blue cells and the preparation of phabs were carried out as described by Barbas III and Lerner, Methods: Companion Methods Enzymol. 2 (1991), 119). The phabs were precipitated with 4% (w/v) polyethylene glycol 8000 and 3% (w/v) NaCl and resuspended in PBS, pH 7.4. The resulting expression library contains $1 \times 10^7$ specificities.

1.6. Isolation of GPIIb/IIIa-specific Phabs

GPIIb/IIIa-specific phabs were prepared by means of a total of 5 rounds of an affinity selection ("panning"). Following preabsorption (negative selection) with $5 \times 10^7$ thrombasthenic platelets, the phabs were incubated for 45 min with $10^8$ normal platelets (positive selection). Bound phabs were then eluted with 0.05 mol/l sodium citrate, pH 2.5, and neutralized with 1 mol/l Tris buffer. After each round of panning, the enrichment of GPIIb/IIIa-specific phabs was monitored by titrating the phage-colony-forming units. After five rounds of selection, the eluted phabs were found to have been enriched by a factor of more than 100.

The pool of phabs obtained after the fourth round of selection was analysed more closely for its GPIIb/IIIa specificity. For this, 40 phab clones were selected at random and their binding specificity was ascertained in an immunodot assay. One $\mu$l of normal and thrombasthenic platelets ($10^9$ ml) [sic], and also purified GPIIb/IIIa (500 $\mu$g/ml), were added as drops onto nitrocellulose strips (Millipore Corporation, Bedford, Mass., USA). The strips were blocked in TBS containing 0.15% casein (TBS-casein) and then incubated overnight together with the phabs, which had been diluted in TBS-casein. After three washes with TBS-0.1% Tween 20 (TBS-Tween), the bound phabs were detected with 4-chloro-l-α-naphthol (Merck, Darmstadt, Germany) following incubation with horseradish peroxidase-conjugated polyclonal rabbit anti-phage antibody (Vogel et al., loc. cit.) which had been diluted 1:1000 in TBS-casein.

The binding of phabs to platelets and purified GPIIb/IIIa was also tested after denaturing the proteins by heating (70° C.) or by acid treatment (pH 2 with 0.5 N HCl) before dropping.

Of the 40 randomly selected clones, 23 (57.5%) reacted with GPIIb/IIIa, whereas 17 did not exhibit any binding. No binding of anti-GPIIb/IIIa [sic] to phabs was observed after denaturing the antigen by heat or pH 2 prior to the incubation, thereby demonstrating that intact GPIIb/IIIa is required for the phab binding. Determining the presence of Fab in negative phabs revealed that 15 of the clones (88%) did not contain any Fab molecules. The two Fab-positive clones which did not bind to GPIIb/IIIa could have a low binding affinity for GPIIb/IIIa.

1.7. Fab Analysis

In order to test the positive phabs for kappa (K), lambda (λ) and Fd chains, the anti-GPIIb/IIIa phabs were added as drops to nitrocellulose. The filters were incubated for 4 hours with peroxidase-labelled mouse anti-human λ, κ (The Binding Site Limited, Birmingham, England) and Fd antibodies (from the HP6045 myeloma cell line, ATCC1757, Rockville, Md., USA), which antibodies had been diluted 1:1000 in TBS-casein, and then developed by chemiluminescence (ECL, Amersham, Switzerland, Zurich, Switzerland). Testing 15 randomly selected anti-GPIIb/IIIa Fab clones for κ, λ and Fd chains showed that an Fd chain was present in 12 of the clones (80%) while the λ chain was present in all the clones.

Fab binding to GPIIb/IIIa on platelets was determined quantitatively by preincubating pool phabs with platelets at various concentrations. The supernatant was then analysed by an immunodot method. In this connection, it was established that from 1 to $3 \times 10^4$ phabs bind per platelet. This indicates that approximately 10 to 50% of the GPIIb/IIIa molecules per platelet can be occupied by phabs.

1.8. Characterizing the Phab-binding Epitopes

The epitope specificity of the phabs was determined by carrying out an inhibition test using a variety of monoclonal antibodies (see item 4 [sic]). 1 $\mu$l of thawed normal and thrombasthenic platelets ($10^9$/ml), purified GPIIb/IIIa (500 $\mu$g/ml), a peptide fragment of GPIIIa (amino acids 468–690, 500 $\mu$g/ml) and the cytoplasmic segment of GPIIb/IIIa (500 $\mu$g/ml) were in each case added as drops, in duplicate, onto nitrocellulose strips. After blocking, the phab clones (0.4 $\mu$g/ml Fab) were incubated overnight with or without monoclonal antibody (1 $\mu$g/ml). The bound phabs were detected using peroxidase-labelled anti-phage antibody and 4-chloro-l-α-naphthol.

Two groups of phab clones were identified in these investigations. While Group A (5 clones) was inhibited moderately by a pool of all the antibodies, it was inhibited strongly by GPIIb/IIIa complex-specific antibodies. Anti-GPIIb antibodies had no effect. While Group B (10 clones) was inhibited completely by the pool of all the antibodies, it was inhibited to a lesser extent by the complex-specific antibody and also by the IIb-specific antibody. No group exhibited any reaction with GPIIIa-specific antibodies. The same results were obtained using either platelets or purified GPIIb/IIIa as the antigen. No phab binding to the cytoplasmic peptide or to the extracellular fragment of GPIIIa was found to occur.

TABLE 1

A summary of these results is shown in Table 1.
Inhibition of phab binding (mean value ± SD in %)

| Pools of monoclonal antibodies for inhibition | Group A phab clones (n = 5) | | Group B phab clones (n = 10) | |
|---|---|---|---|---|
| | Platelets | Purified GPIIb/IIIa | Platelets | Purified GPIIb/IIIa |
| (1) Anti-GPIIB | 0 | 0 | 49.1 ± 5.9 | 49.4 ± 9.2 |
| (2) Anti-GPIIIa | 0 | 0 | 0 | 0 |

TABLE 1-continued

A summary of these results is shown in Table 1.
Inhibition of phab binding (mean value ± SD in %)

| Pools of monoclonal antibodies for | Group A phab clones (n = 5) | | Group B phab clones (n = 10) | |
|---|---|---|---|---|
| inhibition | Platelets | Purified GPIIb/IIIa | Platelets | Purified GPIIb/IIIa |
| (3) Anti-GPIIb/IIIa complex | 77.8 ± 2.9 | 43.6 ± 2.1 | 58.6 ± 4.4 | 45.5 ± 8.0 |
| Pool of all the antibodies (1)–(3) | 47.6 ± 7.7 | 33.0 ± 10.8 | 95.9 ± 2.7 | 97.5 ± 7.5 |

1.9. Inhibition Assays

The blocking, by the anti-GPIIb/IIIa phabs which had been found, of the binding of patient autoantibodies to GPIIb/IIIa was determined by means of inhibition assays. Two of the phab clones which had been identified as previously described (PDG16 and PDG31) were used for this purpose.

Serial dilutions of the eluted patient autoantibodies of from 1:3 to 1:1000 were analysed for binding to purified GPIIb/IIIa. This was done by performing an immunodot assay. 100 ng of purified GPIIb/IIIa were in each case added as drops, in triplicate, onto nitrocellulose strips and the filters were then blocked with TBS-casein. In order to block the binding of AITP autoantibodies to GPIIb/IIIa with phabs, the strips were incubated with $10^{11}$ phabs for 1 h and then incubated with varying dilutions of kITP autoantibodies for 4 h. Bound autoantibodies were detected using peroxidase-labelled anti-human IgG-Fc antibodies and ECL.

Anti-GPIIb/IIIa phabs inhibited the binding of autoantibodies obtained from 8 AITP patients. The inhibition range [sic] was [sic] from 10 to 46%, from 32 to 60% and from 20 to 67% for PTG16, PTG31 and the pool of the two phabs, respectively. These phabs had no effect on the binding of autoantibodies obtained from 4 AITP patients. Both groups contained autoantibodies derived from patients suffering from primary AITP and from disease-associated AITP.

The results which were obtained are summarized in Table 2.

TABLE 2

| | Inhibition of the binding to purified GPIIb/IIIa by (%) | | |
|---|---|---|---|
| AITP patient | Phab clone PDG16 | Phab clone PDG31 | Pool of the two phab clones |
| WS16 | 13 | 19 | 40 |
| WS37 | 14 | 20 | 36 |
| KC | 24 | 22 | 28 |
| KK | 22 | 22 | 40 |
| KP | 10 | 36 | 60 |
| WS2 | 25 | 55 | 65 |
| KS | 60 | 56 | 64 |
| KL | 0 | 15 | 10 |
| KG | 0 | 0 | 0 |
| KM | 0 | 0 | 0 |
| KE | 0 | 0 | 0 |
| KR | 0 | 0 | 0 |

1.10 DNA Sequence Analysis

Plasmid DNA was purified from four Group A phab clones and 4 group [lacuna] clones using the Nukleobond® AX PC 20 purification kit (Macherey-Nagel AG, Oensingen, Switzerland).

The nucleic acid sequencing was carried out on an ABI373A sequencing system using a PRISM Ready Reaction DyeDeoxy Terminator Cycle Sequencing kit. The primers were obtained from Microsynth, Balgach, Switzerland. The following primers were used for sequencing E H chain: Chyl (5'-CGC TGT GCC CCC AGA GGT-3') and PCH (SEQ ID NO:117) (5'-GGC CGC AAA TTC TAT TTC AAG G-3'). The following (SEQ ID NO:118) primers were used for sequencing the L chain: Cλ (5'-GAG ACA CAC CAG TGT GGC-3') (SEQ ID NO:119), Ck (5'-CAC AAC AGA GGC AGT TCC-3') (SEQ ID NO:120) and PCL(5'-CTA AAC TAG CTA GTC TCC-3') (SEQ ID NO:121). The amino acid sequences which were deduced from the DNA sequence were compared with GenEML-Genbank and strain lines were assigned to VH and Vλ families.

The VH and Vλ nucleotide sequences of the 4 phab clones from each group (Group A: PDG7, PDG8, PDG10 and PDG16; Group B: PDG13, PDG17, PDG31 and PTG37 [sic]) were analysed by automated sequencing and compared with known strain line gene sequences (Tables 3 and 4). There was 100% homology in the deduced amino acid sequences of the H and L chains within each group. By contrast, the homology between Group A and Group B was only 36.9% in the case of the H chain and 81.9% in the case of the L chain amino acid sequences.

In the H chain, Group A clones exhibit the highest degree of sequence identity with the strain line gene VH4.11 of the $V_H4$ family (Sanz, et al. EMBO J. 8 (1989), 3741–3748). There were 7 amino acid differences in the framework region (FR) and 8 in the complement-determining [sic] region (CDR). Group B clones differed from the mostly homologous 1.9III strain line sequence of the $V_H3$ family (Berman et al., EMBO J. 7 (1988), 727–738) in four amino acids in the FR and one in the CDR.

In the L chain, the Group A and Group B clones exhibited the highest homology with the DPL2 strain line gene sequence of the $V_{80}$ 1 family (Williams and Winter, Eur. J. Immunol. 323 (1993), 1456). There were nine amino acid differences in FR and ten in CDR in the case of the Group A clones, and one in FR and two in CDR in the case of the Group B clones. The results which were obtained are summarized in Tables 3 and 4.

TABLE 3

A. Heavy Chains

| Clones | SEQ ID | FR1 | SEQ ID | CDR1 | SEQ ID | FR2 |
|---|---|---|---|---|---|---|
| VH4.11 | | QVQLQESGPGLVKPSETLSLTCTVSGGSIS | | SYYWS | | WIRQPPGKGLEWIG |
| PDG7 | 2 | --K-L---------------N-----R--- | | G-S-R | | ----S--------- |
| PDG8 | | ------------------------------ | | ----- | | -------------- |
| PDG10 | | ------------------------------ | | ----- | | -------------- |
| PDG16 | | ------------------------------ | | ----- | | -------------- |
| 1.9III | | QVQLVESGGGVVQPGRSLRLSCAASGFTES | | SYGMH | | WVRQAPGKGLEWVA |
| PDG13 | 6 | --K-L------------------------- | | --A-- | | -------------- |
| PDG17 | | ------------------------------ | | ----- | | -------------- |
| PDG31 | | ------------------------------ | | ----- | | -------------- |
| PDG37 | | ------------------------------ | | ----- | | -------------- |
| H85255 | | ------------------------------ | | ----- | | -------------- |

| Clones | SEQ ID | CDR2 | SEQ ID | FR3 |
|---|---|---|---|---|
| VH4.11 | | YIYYSGSTNYNPSLKS | | RVTISVDTSKNQFSLKLSSVTAADTAVYYCAR |
| PDG7 | | D-S-----K-K---R- | | ---L------------N--------------- |
| PDG8 | | ---------------- | | -------------------------------- |
| PDG10 | | ------------N--- | | -------------------------------- |
| PDG16 | | ------------N--- | | -------------------------------- |
| 1.9III | | VISYDGSNKYYADSVKG | | RFTISRDNSKNTLYLQMNSLRAEDTAVYYCAK |
| PDG13 | | ----------------- | | --A-------------------------R |
| PDG17 | | ----------------- | | -------------------------------- |
| PDG31 | | ------------N---- | | -------------------------------- |
| PDG37 | | ------------N---- | | -------------------------------- |
| H85255 | | ------------N---- | | -------------------------------- |

| Clones | SEQ ID | CDR3 | SEQ ID | FR4 |
|---|---|---|---|---|
| VH4.11 | | | | |
| PDG7 | | VLPFDPISMDV | | WGKGTTVTVSS |
| PDG8 | | VLPFDPISMDV | | WGKGTTVTVSS |
| PDG10 | | VLPFDPISMDV | | WGKGTTVTVSS |
| PDG16 | | VLPFDPISMDV | | WGKGTTVTVSS |
| 1.9III | | | | |
| PDG13 | | ALGSWGGWDHYMDV | | WGKGTTVTVSS |
| PDG17 | | ALGSWGGWDHYMDV | | WGKGTTVTVSS |
| PDG31 | | ALGSWGGWDHYMDV | | WGKGTTVTVSS |
| PDG37 | | ALGSWGGWDHYMDV | | WGKGTTVTVSS |
| H85255 | | DRPIARWTYGGMDV | | WGQGTTVTVSS |

B. Light Chains

| Clones | SEQ ID | FR1 | ID | CDR1 | ID | FR2 | ID | CDR2 |
|---|---|---|---|---|---|---|---|---|
| DPL2 | | VLTQPPSASGTPGQRVTISC | | SGSSSNIGSNTVH | | WYQQLPGTAPKLLIY | | SNNQRPS |
| PDG7 | 4 | -V-----------W----- | | -------R--P-S | | --H-V--------F | | GSH---- |
| PDG8 | | -------------------- | | ------------- | | --------------- | | ------- |
| PDG10 | | -------------------- | | ------------- | | --------------- | | ------- |
| PDG16 | | -------------------- | | ------------- | | --------------- | | ------- |
| DPL2 | | VLTQPPSASGTPGQRVTISC | | SGSSSNIGSNTVN | | WYQQLPGTAPKLLIY | | SNNQRPS |
| PDG13 | 8 | -V------------------ | | ------------- | | --------------- | | ------- |
| PDG17 | | -------------------- | | ------------- | | --------------- | | ------- |
| PDG31 | | -------------------- | | ------------- | | --------------- | | ------- |
| PDG37 | | -------------------- | | ------------- | | --------------- | | ------- |

| Clones | ID | FR3 | ID | CDR3 | ID | FR4 |
|---|---|---|---|---|---|---|
| DPL2 | | GVPDRFSGSKSGTSASLAISGLQSEDEADYYC | | AAWDDSLNG | | |
| PDG7 | | -------------------R----G-AG---- | | -T---G---PV | | FGGGTKLTVLSQP |
| PDG8 | | -------------------------------- | | ----------- | | FGGGTKLTVLSQP |
| PDG10 | | -------------------------------- | | ----------- | | FGGGTKLTVLSQP |
| PDG16 | | -------------------------------- | | ----------- | | FGGGTKLTVLSQP |
| DPL2 | | GVPDRFSGSKSGTSASLAISGLQSEDEADYYC | | AAWDDSLNG | | |
| PDG13 | | -------------------------------- | | ---------WV | | FGGGTKLTVLSQP |
| PDG17 | | -------------------------------- | | ----------- | | FGGGTKLTVLSQP |

TABLE 3-continued

| | | | |
|---|---|---|---|
| PDG31 | ------------------------------- | ---------- | FGGGTKLTVLSQP |
| PDG37 | ------------------------------- | ---------- | FGGGTKLTVLSQP |

FR: Framework region; CDR: complement-determining [sic] region. The top sequences (VH4.11; 1.9III; DPL2) are given for comparative purposes and in each case represent the deduced amino acid sequence for the most closely related published strainline gene sequence. Dashes denote identity. M85255 refers to the EMPL/GenBank reference number and denotes the deduced amino acid sequence of the human anti-GPIIb autoantibody 2E7 (Kunicki et al., J. Autoimmun. 4 (1991), 433–446). In the case of the heavy chain, the first three amino acids (QVK) are specified by the pComb3 vector sequence. The amino acid sequences of the heavy chains of PDG7 and PDG13 are presented in SEQ ID NO:2 and 6, respectively. The amino acid sequences of the light chains of PDG7 and PDG13 are presented in SEQ ID NO:4 and 8, respectively.

Table 4 shows the assignment of the Group A and Group B clones to known strainline V gene sequences in accordance with the amino acid homology

| | Heavy chain | | | Light chain | | |
|---|---|---|---|---|---|---|
| PDG phab clones | $V_H$ family | Strainline gene | Homology (%) | $V_\lambda$ family | Strainline gene | Homology (5) |
| Group A: 7,8,10, 16 | $V_H4$ | $V_{H4}.11$ | 84.3 | $V_\lambda I$ | DPL2 | 81.4 |
| Group B: 13,17, 31,37 | $V_H3$ | 1.9III | 95.1 | $V_\lambda I$ | DPL2 | 97.1 |

2. Identifying Antiidiotypic Antibody Sequences
2.1 Phab Clones AI-X

The phagemids technique was used to identify sequences for antiidiotypic antibodies in accordance with the method described in Example 1. The clone PDG16, which was selected in Example 1, was used as the antigen. There was no negative preselection.

Use was made of a pool of combinatorial phab libraries [lacuna] the specificities of a nonimmune library of peripheral B lymphocytes and of a library of peripheral lymphocytes which had been immobilized with red blood cells, and also of a nonimmune library of B lymphocytes obtained from tonsils.

The pool of phabs which was obtained after the fourth round of panning was analysed. For this, 40 phab clones were selected at random and their binding specificities were determined. 25 of the selected clones reacted with anti-GPIIb/IIIa phab. These antiidioypic phab clones belong to two groups: Group I (three clones) only reacted with Group A autoantibody phab clones (PDG 7, 8, 10 and 16), whereas the Group II phab clones (22 clones in all) reacted with the Group A and Group B phab clones, with murine monoclonal anti-GPIIb/IIIa antibodies, with purified serum immunoglobulin (IVIgG) or F(ab')$_2$ fragments thereof, and with anti-IgE Fab. 14 phab clones (Group III) did not react with any of the substances mentioned. One Group IV phab clone only reacted with anti-GPIIb/IIIa antibodies. The results of these specificity assays are summarized in Table 5a.

A DNA sequence analysis carried out on Group I phab clones (AI-X16, 17 and 24) showed complete identity in the heavy-chain-encoding sequences apart from one amino acid in the CDR2 region and complete identity in the light-chain-encoding sequences. A comparison with known strainline gene sequences showed approx. 85% homology with the VH3 H chain sequence and approx. 90% homology with the V-λII L chain family sequence. A DNA sequence analysis of the H chain gene was carried out on one representative of each of the Group II, III and IV phab clones. The results of this sequence analysis, and of the comparison with known strainline gene sequences, are summarized in Tables 6 and 7a.

The result of an inhibition assay is depicted in FIG. 1. The inhibition of the binding of AI-X17 to PDG-A by purified GPIIb/IIIa was determined by means of an immunodot assay. 660 and 220 ng of PDG-A phab, respectively, were added to nitrocellulose. The antigen was incubated for 2 h with GPIIb/IIIa at concentrations in the range from 50 µg/ml to 50 ng/ml, and with a buffer solution as control, and then incubated for a further two hours with the phage clone AI-X17 (final concentration $10^{12}$/ml). The bound phages were detected using peroxidase-conjungated polyclonal rabbit anti-phage antibody and electrochemiluminescence.

It was found that the AI-X17 phab (Group I) is able to inhibit the binding of Group A antibody phabs (PDG-X) to the IIb/IIIa glycoprotein. This signifies that AI-X17 recognizes the antigen-binding site on PDG-A.

Another clone AI-X2 which binds to PDG-A was sequenced. Like clones AI-X20, 39 and 40, this clone only has a heavy chain and no light chain. The heavy chain is able to bind on its own, possibly as a dimer, to the antigen, i.e. PDG-A, with adequate specificity and affinity.

2.2 Phab Clones AI-B

The phagemid technique was used to identify sequences of other antiidiotypic antibodies in accordance with the method described in Example 2.1. A clone PDG-B which was selected in Example 1 was used as the antigen.

In all, 40 phab clones were selected and their binding specificity determined. 34 of the selected clones reacted with anti-GPIIb/IIIa PHAB. These antiidiotypic phab clones belonged to three groups:

Group I (14 clones) only reacted with the Group B antibody phab clones, whereas the Group II phab clones (8 clones in all) reacted with both Group A and Group B phab clones. The Group III phab clones (12 clones in all) additionally reacted with murine monoclonal anti-GPIIb/IIIa antibodies, with purified serum immunoglobulin (IVIgG) or F(ab')$_2$ fragments thereof, and with anti-IgE Fab. Six phab clones (Group IV) did not react with any of the substances mentioned. The results of these specificity assays are summarized in Table 5b.

The result of carrying out a DNA sequence analysis on Group I phab clones (AI-14, 18, 24 and 38) is summarized in Tables 6 and 7b. Clones AI-B14, 18 and 38 only had a heavy chain.

AI-B14 and 17 are identical. AI-B34 and 40 are likewise identical with AI-B18.

The inhibition of the binding of PDG-B to platelets by AI-B phabs is depicted in FIG. 2. This was determined by means of flow-cytometric analysis. For this, a platelet-rich plasma ($10^7$ platelets in all) was incubated with biotinylated PDG-B in the presence or absence of AI-B phabs and using helper phages as the control. The platelets were fixed with paraformaldehyde and bound PDG-B was detected with R-phycoerythrin (RPE)-labelled streptavidin. 10,000 events were counted in a FACScan appliance and the mean value of the fluorescence (±SD) was recorded. The strongest inhibition (>60%) was achieved with clones AI-B18, 24 and 38. The inhibition of the binding shows that AI-B clones interact with the antigen-binding site on PDG-B.

TABLE 5a

| AIX phab clones | | PDG A | PDGB | anti-IgE Fab | anti-GPIIb/IIIa mAb | SG | F(ab')$_2$ |
|---|---|---|---|---|---|---|---|
| Group I<br>16,17,24 | 3 | + | − | − | − | − | − |
| Group II<br>1,2,3,4,5,6,7,9,11,<br>13,14,23,26,27,28,29,<br>33,35,36,37,38,40 | 22 | + | + | + | + | + | + |
| Group III<br>8,10,12,15,18,19,21,<br>22,25,30,31,32,34,39 | 14 | − | − | − | − | − | − |
| Group IV<br>20 | 1 | − | − | − | + | − | − |

TABLE 5b

| AI-B phab clones | n | PDG-X | PDG-B | anti-IgE Fab | anti-GPIIb/IIIa mAb | IvIgG | IvIgG F(ab')$_2$ |
|---|---|---|---|---|---|---|---|
| (AI-B5,7,8,14,17,<br>18,23,24,30,31,33,<br>34,38,40) | 14 | − | + | − | − | − | − |
| | 8 | + | + | − | − | − | − |
| | 12 | + | + | + | + | + | + |
| | 6 | − | − | − | − | − | − |

TABLE 6

| anti-Id phage clones antiidiotypic phab clones (AI-X and AI-B) | H Chain | | | | L Chain | | | |
|---|---|---|---|---|---|---|---|---|
| | Seq. ID No(s). | $V_H$ family | Straightline Gene | Homology (%)* | Seq. ID No(s). | $V_\lambda$ family | Strainline gene | Homology (%)* |
| AI-X16 | 10, 54, 74, 75, 43 | $V_H$3 | DP47 | 88 | 12, 80, 81 | $V_\lambda$2 | DPL10 | 88 |
| AI-X24 | — | $V_H$3 | DP47 | 88 | — | $V_\lambda$2 | DPL10 | 88 |
| AI-X17 | 76 | $V_H$3 | DP47 | 87 | — | $V_\lambda$2 | DPL10 | 88 |
| AI-X39 | 16, 55, 77, 44 | $V_H$3 | DP49 | 94 | — | — | — | — |
| AI-X40 | 123, 56, 78, 45 | $V_H$3 | DP31 | 95 | — | — | — | — |
| AI-X20 | 14, 57, 79, 46 | $V_H$4 | DP71 | 78 | — | — | — | — |
| AI-B14 | 22, 83, 84, 85 | $V_H$3 | DP46 | 91 | — | — | — | — |
| AI-B17 | — | $V_H$3 | DP46 | 91 | — | — | — | — |
| AI-B18 | 24, 86, 87, 88 | $V_H$1 | DP10 | 85 | — | — | — | — |
| AI-B24 | 26, 127, 88, 89 | $V_H$3 | DP49 | 81 | 122, 116, 99 | $V_\lambda$3 | 3h | 82 |
| AI-B38 | 30, 94, 98, 90 | $V_H$1 | DP5 | 98 | — | — | — | — |

*Highest homology (in %) of the amino acid sequences of the respective phab clones with sequences of known strainline V genes TABLE 7a A. Heavy Chains

| Clones | SEQ ID | FR1 | SEQ ID | CDR1 | SEQ ID | FR2 |
|---|---|---|---|---|---|---|
| DP47 | | EVQLLESGGGLVQPGGSLRLSCAASGFTFS | 103 | SYAMS | | WVRQAPGKGLEWVS |
| AIX16 | 10 | Q-K--------H----------------D | 54 | NF--- | | -------------- |
| AIX24 | | ------------------------------ | | ----- | | -------------- |
| AIX17 | | ------------------------------ | | ----- | | -------------- |

TABLE 7a-continued

| Clones | SEQ ID | FR1 | SEQ ID | CDR1 | FR2 |
|---|---|---|---|---|---|
| DP49 | | QVQLVESGGGVVQPGRSLRLSCAASGFTFS | 104 | SYGMH | WVRQAPGKGLEWVA |
| AIX39 | 16 | --K-L------H---------------- | 55 | --T-- | -------------- |
| DP31 | | EVQLVESGGGLVQPGRSLRLSCAASGFTFD | 105 | DYAMH | WVRQAPGKGLEWVS |
| AIX40 | 123 | --K-L---------------------- | 56 | ---L- | -------------- |
| DP71 | | QVQLQESGPGLVKPSETLSLTCTVSGGSIS | 106 | SYYWS | WIRQPPGKGLEWIG |
| AIX20 | 14 | --K-L-------------------DV--R | 57 | -H--- | -L------------ |

| Clones | SEQ ID | CDR2 | SEQ ID | FR3 |
|---|---|---|---|---|
| DP47 | 107 | AISGSGGSTYYADSVKG | | RFTISRDNSKNTLYLQHNSLRAEDTAVYYCAK |
| AIX16 | 74 | G---G-LL-H------ | 75 | ------N--R--V------------------- |
| AIX24 | | ---------------- | | ------------------------------- |
| AIX17 | 76 | ------------N---- | | ------------------------------- |
| DP49 | 108 | VISYDGSNKYYADSVKG | | RFTISRDNSKNTLYLQMNSLRAEOTAVYYCAK |
| AIX39 | 77 | L---------------- | | --A-----------------K---------- |
| DP31 | 109 | GISWNSGSIGYADSVKG | | RFTISRDNAKNSLYLQMNSLRAEDTALYYCAKD |
| AIX40 | 78 | ----D-T--------- | | -----------------------------V-- |
| DP71 | 110 | YIYYSGSTNYNPSLKS | | RVTISVDTSKNQFSLKLSSVTAADTAVYYCAR |
| AIX20 | 79 | F--DGAR-RF----R- | | --SL-M-P-K------G------S------- |

| Clones | SEQ ID | CDR3 | SEQ ID | FR4 |
|---|---|---|---|---|
| DP47 | | | | |
| AIX16 | 43 | VRDLGYRVLSTFTFDI | | WGQGTKVTVSS |
| AIX24 | | --------------- | | ----------- |
| AIX17 | | --------------- | | ----------- |
| DP49 | | | | |
| AIX39 | 44 | DGRSGSYARFDGMDV | | WGQGTTVTVSS |
| DP31 | | | | |
| AIX40 | 45 | MGSSVVATYNAFDI | | WGQGTMVTVSS |
| DP71 | | | | |
| AIX20 | 46 | DADGDGFSPYYFPY | | WGQGIPVSVSS |

B. Light Chains

| Clones | SEQ ID | FR1 | ID | CDR1 | ID | FR2 | ID | CDR2 |
|---|---|---|---|---|---|---|---|---|
| DPL10 | | QSALTQPASVSGSPGQSITISC | 124 | TGTSSDVGSYNLVS | | WYQQHPGKAPKLMIY | 125 | EVSKRPS |
| AIX16 | 12 | VV-------------------- | 80 | -----AI-N--F-P | | --------------- | 81 | -G----- |
| AIX24 | | --------------------- | | -------------- | | --------------- | | ------- |
| AIX17 | | --------------------- | | -------------- | | --------------- | | ------- |

| Clones | ID | FR3 | ID | CDR3 | ID | FR4 |
|---|---|---|---|---|---|---|
| DPL10 | | GVSNRFSGSKSGNTASLTISGLQAEDEADYYC | 126 | CSYAGSSTF | | |
| AIX16 | | --------------------------E--- | 82 | ---VH---N | | WVFGGGTKLTVLGQPKAAPSVTLFPPSS |
| AIX24 | | ------------------------------- | | --------- | | ---------------------------- |
| AIX17 | | ------------------------------- | | --------- | | ---------------------------- |

FR: Framework region; CDR: complement-determining [sic] region. The top sequences (DP47, DP49, DP31, DP71 and DPL10) are given for comparative purposes and represent the most closely related known strainline sequences. Dashes denote identity. In the case of the heavy chain, the first three amino acids (QVK) are specified by the pComb3 vector sequence. The amino acid sequences of the heavy chains of AIX16, AIX39, AIX40, and AIX20 are presented in SEQ ID NO:10, 16, 123 and 14, respectively. The amino acid sequences of the CDR1 regions of the heavy chains of AIX16, AIX39, AIX40, AIX20, DP47, DP49, DP31 and DP71 are presented in SEQ ID NO:54, 55, 56, 57, 103, 104, 105 and 106, respectively. The amino acid sequences of the CDR2 regions of the heavy chains of AIX16, AIX17, AIX39, AIX40, AIX20, DP47, DP49, DP31 and DP71 are presented in SEQ ID NO:74, 76, 77, 78, 79, 107, 108, 109 and 110, respectively. The amino acid sequence of the light chain of AIX16 is presented in SEQ ID NO:12. The amino acid sequences of the DCR1, CDR2 and CDR3 regions of the AIX16 are presented in SEQ ID NO:80, 81, and 82, respectively. The amino acid sequences of the CDR1, CDR2 and CDR3 regions of DPL10 are presented in SEQ ID NO:124, 125 and 126, respectively.

TABLE 7b

A. Heavy Chains

| Clones | SEQ ID | FR1 | SEQ ID | CDR1 | SEQ ID | FR2 |
|---|---|---|---|---|---|---|
| DP46 | | QVQLVESGGGVVQPGRSLRLSCAASGFTFS | 91 | SYAMH | 95 | WVRQAPGKGLEWVA |
| AI-B14 | 22 | --K-L------------------ | 83 | D-G-- | 84 | -------------- |
| AI-B17 | | ------------------------------ | | ----- | | -------------- |
| DP-10 | | QVQLVQSGAEVKKPGSSVKVSCKASGGTFS | 92 | SYAIS | 96 | WVRQAPGQGLEWMG |
| AI-B18 | 24 | --K-LE------------M----------- | 86 | -HT-- | 87 | -------------- |
| DP-49 | | QVQLVESGGGVVQPGRSLRLSCAASGFTFS | 93 | SYGMH | 97 | WVRQAPGKGLEWVA |
| AI-B24 | 26 | --K-L----L---G------S------N | 127 | K-AI- | 88 | ----------Y-S |
| DP-5 | | QVQLVQSGAEVKKPGASVKVSCKVSGYTLT | 94 | ELSMH | | WVRQAPGKGLEWMG |

TABLE 7b-continued

| | | | | | | | |
|---|---|---|---|---|---|---|---|
| AI-B38 | 30 | Q-K-LE---------------------- | | 94 | ----- | 98 | -------------- |

| Clones | SEQ ID | CDR2 | SEQ ID | FR3 |
|---|---|---|---|---|
| DP46 | | VISYDGSNKYYADSVKG | | RFTISRDNSKNTLYLQMNSLRAEDTAVYYCAR |
| AI-B14 | | A---------------- | | --S------N-------ST---------F--- |
| AI-B17 | | ----------------- | | ------------------------------ |
| DP-10 | | GIIPIFGTANYAQKFQG | | RVTITADESTSTAYMELSSLRSEDTAVYYCAR |
| AI-B18 | | --T-----V-------- | | --------P--------R--T-DDSGI----- |
| DP-49 | | VISYDGSNKYYADSVKG | | RFTISRDNSKNTLYLQMNSLRAEDTAVYYCAK |
| AI-B24 | | A--SN-G-T-------- | | ------------V----S-----------VR |
| DP-5 | | GFDPEDGETIYAQKFQG | | RVTMTEDTSTDTAYMELSSLRSEDTAVYYCAT |
| AI-B38 | | ----------------- | | ------------------------------- |

| Clones | SEQ ID | CDR3 | SEQ ID | FR4 |
|---|---|---|---|---|
| DP46 | | | | |
| AI-B14 | 85 | DSETAIAAAGRFDI | | WGQGTMVTVSS |
| AI-B17 | | -------------- | | ----------- |
| DP-10 | | | | |
| AI-B18 | 88 | EDGTTVPSQPLEF | | WGQGTRVTVSS |
| DP-49 | | | | |
| AI-B24 | 89 | GSGSYLGYYFDY | | WGQGTLVTVSS |
| DP-5 | | | | |
| AI-B38 | 90 | GLRSYNYGRNLDY | | WGQGTLVTVSS |

B. Light Chains

| Clones | SEQ ID | FR1 | ID | CDR1 | ID | FR2 | ID | CDR2 |
|---|---|---|---|---|---|---|---|---|
| VL3h | | SYVLTQPPSVSVAPGKTARITC | 100 | GGNNIGSKSVM | | WYQQKPGQAPVLVIT | 101 | YDSDRPS |
| AI-B24 | | -V---------RQ--T--- | 122 | --YK------- | | -------------V- | 116 | E--Y--- |

| Clones | ID | FR3 | ID | CDR3 | ID | FR4 |
|---|---|---|---|---|---|---|
| VL3h | | FIPERFSGSNSGNTATLTISRVEAGDEADYYC | 102 | QVWSSSSDH | | |
| AI-B24 | | E------------M-----TG----------- | 99 | ----NTN-Q | | TIFGGGTKLTVLRQPKAAPSVTLFPPSS |

FR: Framework region; CDR: complement-determining [sic] region. The top sequences (DP46, DP10, DP49, DP5 and VL3h) are given for comparative purposes and represent the most closely related known strainline sequences. Dashes denote identity. In the case of the heavy chain, the first three amino acids (QVK) are specified by the pComb3 vector sequence. The amino acid sequences of the heavy chains of A-B14, AI-B18, AI-B24 and AI-B38 are presented in SEQ ID NO:22, 24, 26 and 30, respectively. The amino acid sequences of the CDR1 regions of the heavy chains of AI-B14, AI-B18, AI-B24, AI-B38, DP-46, DP-10, DP-49 and DP-5 are presented in SEQ ID NO:83, 86, 127, 94, 91, 92, 93 and 94, respectively. The amino acid sequences of the CDR2 regions of the heavy chains of AI-B14, AI-B18, AI-B24, AI-B38, DP-46, DP-10, DP-49 and DP-5 are presented in SEQ ID NO:84, 87, 88, 98, 95, 96, 97 and 98, respectively. The amino acid sequence of CDR3 regions of the heavy chains of AI-B14, AI-B18, AI-B24, and AI-B38 are presented in SEQ ID NO:85, 88, 89 and 90, respectively. The amino acid sequences of the light chain of AI-B24 is presented in SEQ ID NO:28. The amino acid sequences of the CDR1, CDR2 and CDR3 regions of the light chains of AI-B24 are presented in SEQ ID NO:122, 116 and 99, respectively. The amino acid sequences of the CDR1, CDR2 and CDR3 regions of the light chains of VL3h are presented in SEQ ID NO:100, 101 and 102, respectively.

3. Effect of Autoantibody Polypeptides on the Binding of Fibrinogen to Blood Platelets 3.1 Methods Analysis of the Binding of Fab to EDTA-pretreated Blood Platelets A blood platelet-rich plasma was incubated with 10 mM EDTA for 30 min. Biotinylated PDG-B and PDG-A polypeptides were added and the mixture was incubated at room temperature for 1 h. The binding of PDG-A and PDG-B to blood platelets was measured by flow-cytometric analysis using phycoerythrin-labelled streptavidin.

Aggregation Experiments

Blood platelet-rich plasma ($250\times10^9$/l) was prepared freshly and maintained under 5% $CO_2$. The plasma was activated by different dilutions of ADP (maximum concentration 410 $\mu$M) in the absence or presence of PDG-A or PDG-B (maximum quantity 10 $\mu$g of Fab). The aggregation was measured in a Rodell 300BD-5 aggregometer (Baxter AG, Düidingen, Switzerland). In subsequent experiments, polyclonal anti-Fab antiserum was added to the activated platelets after PDG-A or PDG-B had been added.

Fibrinogen Binding Test

Wells of ELISA plates were coated with 0.5 $\mu$g/ml GPIIb/IIIa and blocked with 3.5% bovine serum albumin in Tris-buffered salt solution. Fibrinogen (Kabi Diagnostics, Stockholm, Sweden) was then added at different concentrations (maximally 0.08 $\mu$g/ml) in the absence or in the presence of PDG-A, PDG-B or anti-IgE Fab as the control (maximum concentration 23 $\mu$g/ml)

The bound fibrinogen was measured with rat anti-human fibrinogen antibody, biotinylated mouse anti-rat antibody and a conjugate consisting of streptavidin and biotinylated horseradish peroxidase (Amersham Pharmacia Biotech Europe GmbH, Dübendorf, Switzerland) and using an ELISA Easy Reader (EAR340AT, SLT Instruments, Austria) at 405 nm.

Competition Assay Using the Monoclonal Antibody 7E3 and the Antibody Fragment ReoPro®

Platelet-rich plasma ($230\times10^9$/l) was incubated for 1.5 h with PDG-B or PDG-A (200 and 400 $\mu$g/ml, respectively) with or without the murine monoclonal antibody 7E3 or its Fab fragment ReoPro® (total quantity of Fab in the range from $10^{14}$ to $10^{19}$). After fixing with an equal volume of 1% paraformaldehyde, the binding of PDG-B and PDG-A to platelets was measured by flow-cytometric analysis using phycoerythrin-labelled streptavidin.

3.2 Results

The recombinant anti-GPIIb/IIIa Fab autoantibody fragments which were tested do not exhibit any binding 9 to blood platelets which had been pretreated with 10 mM EDTA. This shows that the autoantibody fragments only recognize an antigen whose confirmation is intact (FIG. 3).

In aggregation experiments using platelet-enriched plasma, neither PDG-A nor PDG-3 inhibited the aggregation. In a fibrinogen-binding test in which the concentration of fibrinogen was from $10^4$ to $10^6$ times lower than in serum, PDG-A and PDG-B completely inhibited the fibrinogen binding (FIG. 4). No inhibition occurred when anti-IgE Fab, which had been obtained by a similar enrichment protocol, was used as the control. These results show that both PDG-A and PDG-B interact powerfully with the fibrinogen-binding site on GPIIb/IIIa.

In investigations carried out with the murine monoclonal anti-GPIIb/IIIa antibody 7E3 and its commercially available Fab fragment ReoPro®, both of which inhibit the binding of fibrinogen to activated GPIIb/IIIa, the binding of PDG-B to blood platelets was found to be inhibited selectively and completely (FIGS. 5 to 7). By contrast, the binding of PDG-A to blood platelets was not inhibited significantly either by 7E3 or by ReoPro®.

What is claimed:

1. An isolated human antibody or antigen binding fragment thereof which is able to bind to a GPIIb/IIIa complex, wherein the heavy chain of said antibody or antigen binding fragment comprises a CDR3 region a CDR2 region and a CDR1 region, wherein said CDR3 region is encoded by a nucleotide sequence selected from the group consisting of:

(a) a nucleotide sequence which encodes the amino acid sequence: VLPFDPISMDV (SEQ ID NO:31), and
   (b) a nucleotide sequence which encodes the amino acid sequence ALGSWGGWDHYMDV (SEQ ID NO:32), and said CDR1 region is encoded by a nucleotide sequence selected from the group consisting of:

(c) a nucleotide sequence which encodes the amino acid sequence: GYSWR (SEQ ID NO: 33), and
   (d) a nucleotide sequence which encodes the amino acid sequence: SYAMH (SEQ ID NO: 34), and said CDR2 region is encoded by a nucleotide sequence selected from the group consisting of:

(e) a nucleotide sequence which encodes the amino acid sequence: DISYSGSTKYKPSLRS (SEQ ID NO: 35), and
   (f) a nucleotide sequence which encodes the amino acid sequence: VISYDGSNKYYADSVKG (SEQ ID NO: 36).

2. The antibody or antigen binding fragment according to claim 1, wherein it is coupled to a detectable labeling group or a toxin.

3. A composition comprising an antibody or antigen binding fragment according to claim 1, in combination with adjuvants, additives or excipients.

4. The antibody or antigen binding fragment according to claim 1, further comprising a light or antigen binding fragment thereof, wherein said antibody or antigen binding fragment thereof is able to bind to GPIIb/IIIa, and wherein the light chain comprises a CDR3 region, a CDR2 region and a CDR1 region, wherein said CDR3 region is encoded by a nucleotide sequence selected from the group consisting of:

(a) a nucleotide sequence which encodes the amino acid sequence: ATWDDGLNGPV (SEQ ID NO:37), and
   (b) a nucleotide sequence which encodes the amino acid sequence AAWDDSLNGWV (SEQ ID NO:38), and said CDR1 region is encoded by a nucleotide sequence selected from the group consisting of:

(c) a nucleotide sequence which encodes the amino acid sequence: SGSSSNIRSNPVS (SEQ ID NO: 39), and
   (d) a nucleotide sequence which encodes the amino acid sequence: SGSSSNIGSNTVN (SEQ ID NO: 40), and said CDR2 region is encoded by a nucleotide sequence selected from the group consisting of:

(e) a nucleotide sequence which encodes the amino acid sequence: GSHQRPS (SEQ ID NO: 4 1), and
   (f) a nucleotide sequence which encodes the amino acid sequence: SNNQRPS (SEQ ID NO: 42).

5. A composition comprising an antibody or antigen binding fragment according to claim 4 in combination with adjuvants, additives or excipients.

* * * * *